(12) United States Patent
Erickson-Miller et al.

(10) Patent No.: US 6,998,124 B1
(45) Date of Patent: Feb. 14, 2006

(54) ERYTHROPOIETIN RECEPTOR ANTIBODIES

(75) Inventors: Connie L. Erickson-Miller, Exton, PA (US); Stephen D. Holmes, Harlow (GB); Alexander H. Taylor, Exton, PA (US); Peter R. Young, Wilmington, DE (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/958,620

(22) PCT Filed: Apr. 14, 2000

(86) PCT No.: PCT/US00/10284

§ 371 (c)(1),
(2), (4) Date: Oct. 12, 2001

(87) PCT Pub. No.: WO00/61637

PCT Pub. Date: Oct. 19, 2000

Related U.S. Application Data

(60) Provisional application No. 60/129,263, filed on Apr. 14, 1999.

(51) Int. Cl.
  *C07K 16/28* (2006.01)
  *A61K 39/395* (2006.01)
(52) U.S. Cl. ............................. 424/143.1; 424/130.1; 424/141.1; 530/387.1; 530/388.1; 530/388.22; 530/387.3
(58) Field of Classification Search ............ 530/387.1, 530/388.1, 388.22, 387.3; 424/130.1, 141.1, 424/143.1
See application file for complete search history.

(56) References Cited

U.S. PATENT DOCUMENTS 5,843,726 A   12/1998  Lee .......................... 435/69.7

*Primary Examiner*—Prema Mertz
(74) *Attorney, Agent, or Firm*—Edward R. Gimmi; Charles M. Kinzig

(57) ABSTRACT

Erythropoietin receptor agonist and antagonist antibodies and their use in enhancing erythropoiesis are disclosed.

16 Claims, 9 Drawing Sheets

SEQUENCE LISTING

<160> NUMBER OF SEQ ID NOS: 23

<210> SEQ ID NO 1
<211> LENGTH: 360
<212> TYPE: DNA
<213> ORGANISM: Artificial Sequence
<220> FEATURE:
<221> NAME/KEY: CDS
<222> LOCATION: (1)...(360)
<223> OTHER INFORMATION: 3G9 heavy chain variable region

<400> SEQUENCE: 1

```
caa gtt cag ctt caa cag cct ggg gct gag ctt gtg aag tct ggg gcc        48
Gln Val Gln Leu Gln Gln Pro Gly Ala Glu Leu Val Lys Ser Gly Ala
1               5                   10                  15 tca gtg aag ctg tcc tgc aag gct tct ggc agt acc ttc acc agc tac        96
Ser Val Lys Leu Ser Cys Lys Ala Ser Gly Ser Thr Phe Thr Ser Tyr
            20                  25                  30 tgg atg cac tgg gtg aag cag agg cct gga cga ggc ctt gag tgg att       144
Trp Met His Trp Val Lys Gln Arg Pro Gly Arg Gly Leu Glu Trp Ile
        35                  40                  45 gga agg att gat cca aat agt ggt ggt act aag gat aat gag aag ttc       192
Gly Arg Ile Asp Pro Asn Ser Gly Gly Thr Lys Asp Asn Glu Lys Phe
    50                  55                  60 aag agc aag gcc aca ctg act gta gac aaa ccc tcc agc aca gcc tac       240
Lys Ser Lys Ala Thr Leu Thr Val Asp Lys Pro Ser Ser Thr Ala Tyr
65                  70                  75                  80 atg cag ctc agc agc ctg aca tct gag gac tct gcg gtc tat tat tgt       288
Met Gln Leu Ser Ser Leu Thr Ser Glu Asp Ser Ala Val Tyr Tyr Cys
                85                  90                  95 gca aga gag acc tac tat gat tcc tcg ttt gct tac tgg ggc caa ggg       336
Ala Arg Glu Thr Tyr Tyr Asp Ser Ser Phe Ala Tyr Trp Gly Gln Gly
            100                 105                 110 act ctg gtc act gtc tct gca gcc                                       360
Thr Leu Val Thr Val Ser Ala Ala
        115                 120
```

<210> SEQ ID NO 2
<211> LENGTH: 120
<212> TYPE: PRT
<213> ORGANISM: Artificial Sequence
<220> FEATURE:
<223> OTHER INFORMATION: 3G9 heavy chain variable region

<400> SEQUENCE: 2

```
Gln Val Gln Leu Gln Gln Pro Gly Ala Glu Leu Val Lys Ser Gly Ala
1               5                   10                  15

Ser Val Lys Leu Ser Cys Lys Ala Ser Gly Ser Thr Phe Thr Ser Tyr
            20                  25                  30
```

```
Trp Met His Trp Val Lys Gln Arg Pro Gly Arg Gly Leu Glu Trp Ile
         35                  40                  45

Gly Arg Ile Asp Pro Asn Ser Gly Gly Thr Lys Asp Asn Glu Lys Phe
     50                  55                  60

Lys Ser Lys Ala Thr Leu Thr Val Asp Lys Pro Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Glu Thr Tyr Tyr Asp Ser Ser Phe Ala Tyr Trp Gly Gln Gly
             100                 105                 110

Thr Leu Val Thr Val Ser Ala Ala
         115                 120

<210> SEQ ID NO 3
<211> LENGTH: 336
<212> TYPE: DNA
<213> ORGANISM: Artificial Sequence
<220> FEATURE:
<221> NAME/KEY: CDS
<222> LOCATION: (1)...(336)
<223> OTHER INFORMATION: 3G9 light chain variable region

<400> SEQUENCE: 3 gat att gtt atg act cag tct caa aaa ttc atg tcc aca tca gta gga      48
Asp Ile Val Met Thr Gln Ser Gln Lys Phe Met Ser Thr Ser Val Gly
 1               5                  10                  15 gac agg gtc agc gtc acc tgc aag gcc agt cag aat gtg ggt act aat     96
Asp Arg Val Ser Val Thr Cys Lys Ala Ser Gln Asn Val Gly Thr Asn
             20                  25                  30 gta gcc tgg tat caa cag aaa cca ggg caa tct cct aaa gca ctg att    144
Val Ala Trp Tyr Gln Gln Lys Pro Gly Gln Ser Pro Lys Ala Leu Ile
         35                  40                  45 tac tcg gca tcc tac cgg tac agt gga gtc cct gat cgc ttc aca ggc    192
Tyr Ser Ala Ser Tyr Arg Tyr Ser Gly Val Pro Asp Arg Phe Thr Gly
     50                  55                  60 agt gga tct ggg aca gat ttc act ctc acc atc agc aat gtg cag tct    240
Ser Gly Ser Gly Thr Asp Phe Thr Leu Thr Ile Ser Asn Val Gln Ser
 65                  70                  75                  80 gaa gac ttg gca gag tat ttc tgt cag caa tat aac agc tat cct ctc    288
Glu Asp Leu Ala Glu Tyr Phe Cys Gln Gln Tyr Asn Ser Tyr Pro Leu
                 85                  90                  95 acg ttc ggt gct ggg acc aag ctg gag ctg aaa cgg gct gat gct gca    336
Thr Phe Gly Ala Gly Thr Lys Leu Glu Leu Lys Arg Ala Asp Ala Ala
             100                 105                 110

<210> SEQ ID NO 4
<211> LENGTH: 112
<212> TYPE: PRT
<213> ORGANISM: Artificial Sequence
<220> FEATURE:
<223> OTHER INFORMATION: 3G9 light chain variable region

<400> SEQUENCE: 4

Asp Ile Val Met Thr Gln Ser Gln Lys Phe Met Ser Thr Ser Val Gly
 1               5                  10                  15

Asp Arg Val Ser Val Thr Cys Lys Ala Ser Gln Asn Val Gly Thr Asn
             20                  25                  30

Val Ala Trp Tyr Gln Gln Lys Pro Gly Gln Ser Pro Lys Ala Leu Ile
         35                  40                  45

Tyr Ser Ala Ser Tyr Arg Tyr Ser Gly Val Pro Asp Arg Phe Thr Gly
     50                  55                  60
```

```
Ser Gly Ser Gly Thr Asp Phe Thr Leu Thr Ile Ser Asn Val Gln Ser
 65                  70                  75                  80

Glu Asp Leu Ala Glu Tyr Phe Cys Gln Gln Tyr Asn Ser Tyr Pro Leu
                 85                  90                  95

Thr Phe Gly Ala Gly Thr Lys Leu Glu Leu Lys Arg Ala Asp Ala Ala
            100                 105                 110

<210> SEQ ID NO 5
<211> LENGTH: 5
<212> TYPE: PRT
<213> ORGANISM: Homo sapiens

<400> SEQUENCE: 5

Ser Tyr Trp Met His
 1               5

<210> SEQ ID NO 6
<211> LENGTH: 17
<212> TYPE: PRT
<213> ORGANISM: Homo sapiens

<400> SEQUENCE: 6

Arg Ile Asp Pro Asn Ser Gly Gly Thr Lys Asp Asn Glu Lys Phe Lys
 1               5                  10                  15

Ser

<210> SEQ ID NO 7
<211> LENGTH: 10
<212> TYPE: PRT
<213> ORGANISM: Homo sapiens

<400> SEQUENCE: 7

Glu Thr Tyr Tyr Asp Ser Ser Phe Ala Tyr
 1               5                  10

<210> SEQ ID NO 8
<211> LENGTH: 11
<212> TYPE: PRT
<213> ORGANISM: Homo sapiens

<400> SEQUENCE: 8

Lys Ala Ser Gln Asn Val Gly Thr Asn Val Ala
 1               5                  10

<210> SEQ ID NO 9
<211> LENGTH: 7
<212> TYPE: PRT
<213> ORGANISM: Homo sapiens

<400> SEQUENCE: 9

Ser Ala Ser Tyr Arg Tyr Ser
 1               5

<210> SEQ ID NO 10
<211> LENGTH: 9
<212> TYPE: PRT
<213> ORGANISM: Homo sapiens

<400> SEQUENCE: 10

Gln Gln Tyr Asn Ser Tyr Pro Leu Thr
 1               5
```

<210> SEQ ID NO 11
<211> LENGTH: 375
<212> TYPE: DNA
<213> ORGANISM: Homo sapiens
<220> FEATURE:
<221> NAME/KEY: CDS
<222> LOCATION: (1)...(375)

<400> SEQUENCE: 11

| acc | ggt | gtc | cac | tcc | caa | gtc | cag | ctt | gta | cag | tct | ggg | gct | gag | gtt | 48 |
| Thr | Gly | Val | His | Ser | Gln | Val | Gln | Leu | Val | Gln | Ser | Gly | Ala | Glu | Val | |
| 1 | | | | 5 | | | | | 10 | | | | | 15 | | |

| aag | aag | cct | ggg | gcc | tca | gtg | aag | gtg | tcc | tgt | aag | gct | tct | ggc | agt | 96 |
| Lys | Lys | Pro | Gly | Ala | Ser | Val | Lys | Val | Ser | Cys | Lys | Ala | Ser | Gly | Ser | |
| | | | 20 | | | | | 25 | | | | | 30 | | | |

| acc | ttc | acc | agc | tac | tgg | atg | cac | tgg | gtg | aag | cag | gcg | cct | gga | caa | 144 |
| Thr | Phe | Thr | Ser | Tyr | Trp | Met | His | Trp | Val | Lys | Gln | Ala | Pro | Gly | Gln | |
| | | | 35 | | | | | 40 | | | | | 45 | | | |

| ggc | ctt | gag | tgg | att | gga | agg | att | gat | cca | aat | agt | ggt | ggt | act | aag | 192 |
| Gly | Leu | Glu | Trp | Ile | Gly | Arg | Ile | Asp | Pro | Asn | Ser | Gly | Gly | Thr | Lys | |
| | 50 | | | | | 55 | | | | | 60 | | | | | |

| gat | aat | gag | aag | ttc | aag | agc | aag | gcc | aca | ctg | act | gta | gac | aaa | tcc | 240 |
| Asp | Asn | Glu | Lys | Phe | Lys | Ser | Lys | Ala | Thr | Leu | Thr | Val | Asp | Lys | Ser | |
| 65 | | | | 70 | | | | | 75 | | | | | 80 | | |

| acc | agc | aca | gcc | tac | atg | gag | ctc | agc | agc | ctg | aga | tct | gag | gac | act | 288 |
| Thr | Ser | Thr | Ala | Tyr | Met | Glu | Leu | Ser | Ser | Leu | Arg | Ser | Glu | Asp | Thr | |
| | | | 85 | | | | | 90 | | | | | 95 | | | |

| gcg | gtc | tat | tat | tgt | gca | aga | gag | acc | tac | tat | gat | tcc | tcg | ttt | gct | 336 |
| Ala | Val | Tyr | Tyr | Cys | Ala | Arg | Glu | Thr | Tyr | Tyr | Asp | Ser | Ser | Phe | Ala | |
| | | | 100 | | | | | 105 | | | | | 110 | | | |

| tac | tgg | ggc | caa | ggg | act | atg | gtc | act | gtc | tct | gca | gct | | | | 375 |
| Tyr | Trp | Gly | Gln | Gly | Thr | Met | Val | Thr | Val | Ser | Ala | Ala | Ala | Ala | | |
| | | 115 | | | | | 120 | | | | | 125 | | | | |

<210> SEQ ID NO 12
<211> LENGTH: 128
<212> TYPE: PRT
<213> ORGANISM: Homo sapiens

<400> SEQUENCE: 12

| Thr | Gly | Val | His | Ser | Gln | Val | Gln | Leu | Val | Gln | Ser | Gly | Ala | Glu | Val |
| 1 | | | | 5 | | | | | 10 | | | | | 15 | |

| Lys | Lys | Pro | Gly | Ala | Ser | Val | Lys | Val | Ser | Cys | Lys | Ala | Ser | Gly | Ser |
| | | | 20 | | | | | 25 | | | | | 30 | | |

| Thr | Phe | Thr | Ser | Tyr | Trp | Met | His | Trp | Val | Lys | Gln | Ala | Pro | Gly | Gln |
| | | | 35 | | | | | 40 | | | | | 45 | | |

| Gly | Leu | Glu | Trp | Ile | Gly | Arg | Ile | Asp | Pro | Asn | Ser | Gly | Gly | Thr | Lys |
| | 50 | | | | | 55 | | | | | 60 | | | | |

| Asp | Asn | Glu | Lys | Phe | Lys | Ser | Lys | Ala | Thr | Leu | Thr | Val | Asp | Lys | Ser |
| 65 | | | | 70 | | | | | 75 | | | | | 80 | | |

| Thr | Ser | Thr | Ala | Tyr | Met | Glu | Leu | Ser | Ser | Leu | Arg | Ser | Glu | Asp | Thr |
| | | | 85 | | | | | 90 | | | | | 95 | | |

| Ala | Val | Tyr | Tyr | Cys | Ala | Arg | Glu | Thr | Tyr | Tyr | Asp | Ser | Ser | Phe | Ala |
| | | | 100 | | | | | 105 | | | | | 110 | | |

| Tyr | Trp | Gly | Gln | Gly | Thr | Met | Val | Thr | Val | Ser | Ala | Ala | Ala | Ala | |
| | | 115 | | | | | 120 | | | | | 125 | | | |

<210> SEQ ID NO 13
<211> LENGTH: 375
<212> TYPE: DNA
<213> ORGANISM: Artificial Sequence -continued

```
<220> FEATURE:
<221> NAME/KEY: CDS
<222> LOCATION: (1)...(375)
<223> OTHER INFORMATION: sequence reflecting construct 3G9HZHCS14

<400> SEQUENCE: 13 acc ggt gtc cac tcc caa gtc cag ctt gta cag tct ggg gct gag gtt       48
Thr Gly Val His Ser Gln Val Gln Leu Val Gln Ser Gly Ala Glu Val
 1               5                  10                  15 aag aag tct ggg gcc tca gtg aag gtg tcc tgt aag gct tct ggc agt       96
Lys Lys Ser Gly Ala Ser Val Lys Val Ser Cys Lys Ala Ser Gly Ser
                20                  25                  30 acc ttc acc agc tac tgg atg cac tgg gtg aag cag gcg cct gga caa      144
Thr Phe Thr Ser Tyr Trp Met His Trp Val Lys Gln Ala Pro Gly Gln
            35                  40                  45 ggc ctt gag tgg att gga agg att gat cca aat agt ggt ggt act aag      192
Gly Leu Glu Trp Ile Gly Arg Ile Asp Pro Asn Ser Gly Gly Thr Lys
        50                  55                  60 gat aat gag aag ttc aag agc aag gcc aca ctg act gta gac aaa tcc      240
Asp Asn Glu Lys Phe Lys Ser Lys Ala Thr Leu Thr Val Asp Lys Ser
 65                 70                  75                  80 acc agc aca gcc tac atg gag ctc agc agc ctg aga tct gag gac act      288
Thr Ser Thr Ala Tyr Met Glu Leu Ser Ser Leu Arg Ser Glu Asp Thr
                85                  90                  95 gcg gtc tat tat tgt gca aga gag acc tac tat gat tcg tcg ttt gct      336
Ala Val Tyr Tyr Cys Ala Arg Glu Thr Tyr Tyr Asp Ser Ser Phe Ala
            100                 105                 110 tac tgg ggc caa ggg act atg gtc act gtc tct gca gct                  375
Tyr Trp Gly Gln Gly Thr Met Val Thr Val Ser Ala Ala Ala Ala Ala
        115                 120                 125

<210> SEQ ID NO 14
<211> LENGTH: 128
<212> TYPE: PRT
<213> ORGANISM: Artificial Sequence
<220> FEATURE:
<223> OTHER INFORMATION: sequence reflecting construct 3G9HZHCS14

<400> SEQUENCE: 14

Thr Gly Val His Ser Gln Val Gln Leu Val Gln Ser Gly Ala Glu Val
 1               5                  10                  15

Lys Lys Ser Gly Ala Ser Val Lys Val Ser Cys Lys Ala Ser Gly Ser
                20                  25                  30

Thr Phe Thr Ser Tyr Trp Met His Trp Val Lys Gln Ala Pro Gly Gln
            35                  40                  45

Gly Leu Glu Trp Ile Gly Arg Ile Asp Pro Asn Ser Gly Gly Thr Lys
        50                  55                  60

Asp Asn Glu Lys Phe Lys Ser Lys Ala Thr Leu Thr Val Asp Lys Ser
 65                 70                  75                  80

Thr Ser Thr Ala Tyr Met Glu Leu Ser Ser Leu Arg Ser Glu Asp Thr
                85                  90                  95

Ala Val Tyr Tyr Cys Ala Arg Glu Thr Tyr Tyr Asp Ser Ser Phe Ala
            100                 105                 110

Tyr Trp Gly Gln Gly Thr Met Val Thr Val Ser Ala Ala Ala Ala Ala
        115                 120                 125

<210> SEQ ID NO 15
<211> LENGTH: 324
<212> TYPE: DNA
<213> ORGANISM: Artificial Sequence
```

```
<220> FEATURE:
<221> NAME/KEY: CDS
<222> LOCATION: (1)...(324)
<223> OTHER INFORMATION: light chain variable region 3G9HZLC1-0

<400> SEQUENCE: 15 gct acc ggt gtc cac tcc gat att gtc atg act cag tct cca tca tcc      48
Ala Thr Gly Val His Ser Asp Ile Val Met Thr Gln Ser Pro Ser Ser
 1               5                  10                  15 ctg tcc gca tca gta gga gac agg gtc acc atc acc tgc aaa gct tct      96
Leu Ser Ala Ser Val Gly Asp Arg Val Thr Ile Thr Cys Lys Ala Ser
             20                  25                  30 cag aat gtg ggt act aat gta gcc tgg tat caa cag aaa cca ggg aaa     144
Gln Asn Val Gly Thr Asn Val Ala Trp Tyr Gln Gln Lys Pro Gly Lys
         35                  40                  45 gct cct aaa gca ctg att tac tcg gca tcc tat cgg tac agt gga gtc     192
Ala Pro Lys Ala Leu Ile Tyr Ser Ala Ser Tyr Arg Tyr Ser Gly Val
     50                  55                  60 cct gat cgc ttc tca ggc agt gga tcc ggg aca gat ttc act ctc acc     240
Pro Asp Arg Phe Ser Gly Ser Gly Ser Gly Thr Asp Phe Thr Leu Thr
 65                  70                  75                  80 atc agc agt ctg cag cct gaa gac ttc gca acg tat tac tgt cag caa     288
Ile Ser Ser Leu Gln Pro Glu Asp Phe Ala Thr Tyr Tyr Cys Gln Gln
                 85                  90                  95 tat aac agc tat cct ctc acg ttc ggt ggt ggt acc                     324
Tyr Asn Ser Tyr Pro Leu Thr Phe Gly Gly Gly Thr
            100                 105

<210> SEQ ID NO 16
<211> LENGTH: 108
<212> TYPE: PRT
<213> ORGANISM: Artificial Sequence
<220> FEATURE:
<223> OTHER INFORMATION: light chain variable region 3G9HZLC1-0

<400> SEQUENCE: 16

Ala Thr Gly Val His Ser Asp Ile Val Met Thr Gln Ser Pro Ser Ser
 1               5                  10                  15

Leu Ser Ala Ser Val Gly Asp Arg Val Thr Ile Thr Cys Lys Ala Ser
             20                  25                  30

Gln Asn Val Gly Thr Asn Val Ala Trp Tyr Gln Gln Lys Pro Gly Lys
         35                  40                  45

Ala Pro Lys Ala Leu Ile Tyr Ser Ala Ser Tyr Arg Tyr Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Tyr Asn Ser Tyr Pro Leu Thr Phe Gly Gly Gly Thr
            100                 105

<210> SEQ ID NO 17
<211> LENGTH: 324
<212> TYPE: DNA
<213> ORGANISM: Homo sapiens
<220> FEATURE:
<221> NAME/KEY: CDS
<222> LOCATION: (1)...(324)
```

```
<400> SEQUENCE: 17 gct acc ggt gtc cac tcc gat att gtc atg act cag tct cca tca tcc        48
Ala Thr Gly Val His Ser Asp Ile Val Met Thr Gln Ser Pro Ser Ser
  1               5                  10                  15 ctg tcc gca tca gta gga gac agg gtc acc atc acc tgc aaa gct tct        96
Leu Ser Ala Ser Val Gly Asp Arg Val Thr Ile Thr Cys Lys Ala Ser
                 20                  25                  30 cag aat gtg ggt act aat gta gcc tgg tat caa cag aaa cca ggg aaa       144
Gln Asn Val Gly Thr Asn Val Ala Trp Tyr Gln Gln Lys Pro Gly Lys
             35                  40                  45 gct cct aaa gca ctg att tac tcg gca tcc tat cgg tac agt gga gtc       192
Ala Pro Lys Ala Leu Ile Tyr Ser Ala Ser Tyr Arg Tyr Ser Gly Val
         50                  55                  60 cct gat cgc ttc tca ggc agt gga tcc ggg aca gat ttc act ttc acc       240
Pro Asp Arg Phe Ser Gly Ser Gly Ser Gly Thr Asp Phe Thr Phe Thr
 65                  70                  75                  80 atc agc agt ctg cag cct gaa gac atc gca acg tat tac tgt cag caa       288
Ile Ser Ser Leu Gln Pro Glu Asp Ile Ala Thr Tyr Tyr Cys Gln Gln
                 85                  90                  95 tat aac agc tat cct ctc acg ttc ggt ggt ggt acc                       324
Tyr Asn Ser Tyr Pro Leu Thr Phe Gly Gly Gly Thr
            100                 105

<210> SEQ ID NO 18
<211> LENGTH: 108
<212> TYPE: PRT
<213> ORGANISM: Homo sapiens

<400> SEQUENCE: 18

Ala Thr Gly Val His Ser Asp Ile Val Met Thr Gln Ser Pro Ser Ser
  1               5                  10                  15

Leu Ser Ala Ser Val Gly Asp Arg Val Thr Ile Thr Cys Lys Ala Ser
                 20                  25                  30

Gln Asn Val Gly Thr Asn Val Ala Trp Tyr Gln Gln Lys Pro Gly Lys
             35                  40                  45

Ala Pro Lys Ala Leu Ile Tyr Ser Ala Ser Tyr Arg Tyr Ser Gly Val
         50                  55                  60

Pro Asp Arg Phe Ser Gly Ser Gly Ser Gly Thr Asp Phe Thr Phe Thr
 65                  70                  75                  80

Ile Ser Ser Leu Gln Pro Glu Asp Ile Ala Thr Tyr Tyr Cys Gln Gln
                 85                  90                  95

Tyr Asn Ser Tyr Pro Leu Thr Phe Gly Gly Gly Thr
            100                 105

<210> SEQ ID NO 19
<211> LENGTH: 324
<212> TYPE: DNA
<213> ORGANISM: Homo sapiens
<220> FEATURE:
<221> NAME/KEY: CDS
<222> LOCATION: (1)...(324)

<400> SEQUENCE: 19 gct acc ggt gtc cac tcc gat att gtc atg act cag tct cca tca tcc        48
Ala Thr Gly Val His Ser Asp Ile Val Met Thr Gln Ser Pro Ser Ser
  1               5                  10                  15 ctg tcc gca tca gta gga gac agg gtc acc atc acc tgc aaa gct tct        96
Leu Ser Ala Ser Val Gly Asp Arg Val Thr Ile Thr Cys Lys Ala Ser
                 20                  25                  30
```

```
cag aat gtg ggt act aat gta gcc tgg tat caa cag aaa cca ggg aaa      144
Gln Asn Val Gly Thr Asn Val Ala Trp Tyr Gln Gln Lys Pro Gly Lys
        35                  40                  45 gct cct aaa gca ctg att tac tcg gca tcc tat cgg tac agt gga gtc      192
Ala Pro Lys Ala Leu Ile Tyr Ser Ala Ser Tyr Arg Tyr Ser Gly Val
 50                  55                  60 cct gat cgc ttc tca ggc agt gga tcc ggg aca gat ttc act ttc acc      240
Pro Asp Arg Phe Ser Gly Ser Gly Ser Gly Thr Asp Phe Thr Phe Thr
 65                  70                  75                  80 atc agc agt ctg cag cct gaa gac ttc gca acg tat tac tgt cag caa      288
Ile Ser Ser Leu Gln Pro Glu Asp Phe Ala Thr Tyr Tyr Cys Gln Gln
                 85                  90                  95 tat aac agc tat cct ctc acg ttc ggt ggt ggt acc                      324
Tyr Asn Ser Tyr Pro Leu Thr Phe Gly Gly Gly Thr
                100                 105

<210> SEQ ID NO 20
<211> LENGTH: 108
<212> TYPE: PRT
<213> ORGANISM: Homo sapiens

<400> SEQUENCE: 20

Ala Thr Gly Val His Ser Asp Ile Val Met Thr Gln Ser Pro Ser Ser
 1               5                  10                  15

Leu Ser Ala Ser Val Gly Asp Arg Val Thr Ile Thr Cys Lys Ala Ser
             20                  25                  30

Gln Asn Val Gly Thr Asn Val Ala Trp Tyr Gln Gln Lys Pro Gly Lys
         35                  40                  45

Ala Pro Lys Ala Leu Ile Tyr Ser Ala Ser Tyr Arg Tyr Ser Gly Val
 50                  55                  60

Pro Asp Arg Phe Ser Gly Ser Gly Ser Gly Thr Asp Phe Thr Phe Thr
 65                  70                  75                  80

Ile Ser Ser Leu Gln Pro Glu Asp Phe Ala Thr Tyr Tyr Cys Gln Gln
                 85                  90                  95

Tyr Asn Ser Tyr Pro Leu Thr Phe Gly Gly Gly Thr
                100                 105

<210> SEQ ID NO 21
<211> LENGTH: 324
<212> TYPE: DNA
<213> ORGANISM: Homo sapiens
<220> FEATURE:
<221> NAME/KEY: CDS
<222> LOCATION: (1)...(324)

<400> SEQUENCE: 21 gct acc ggt gtc cac tcc gat att gtc atg act cag tct cca tca tcc       48
Ala Thr Gly Val His Ser Asp Ile Val Met Thr Gln Ser Pro Ser Ser
 1               5                  10                  15 ctg tcc gca tca gta gga gac agg gtc acc atc acc tgc aaa gct tct       96
Leu Ser Ala Ser Val Gly Asp Arg Val Thr Ile Thr Cys Lys Ala Ser
             20                  25                  30 cag aat gtg ggt act aat gta gcc tgg tat caa cag aaa cca ggg aaa      144
Gln Asn Val Gly Thr Asn Val Ala Trp Tyr Gln Gln Lys Pro Gly Lys
         35                  40                  45 gct cct aaa gca ctg att tac tcg gca tcc tat cgg tac agt gga gtc      192
Ala Pro Lys Ala Leu Ile Tyr Ser Ala Ser Tyr Arg Tyr Ser Gly Val
 50                  55                  60
```

```
cct gat cgc ttc tca ggc agt gga tcc ggg aca gat ttc act ctc acc      240
Pro Asp Arg Phe Ser Gly Ser Gly Ser Gly Thr Asp Phe Thr Leu Thr
 65              70                  75                  80 atc agc agt ctg cag cct gaa gac atc gca acg tat tac tgt cag caa      288
Ile Ser Ser Leu Gln Pro Glu Asp Ile Ala Thr Tyr Tyr Cys Gln Gln
                 85                  90                  95 tat aac agc tat cct ctc acg ttc ggt ggt ggt acc                      324
Tyr Asn Ser Tyr Pro Leu Thr Phe Gly Gly Gly Thr
                100                 105
```

<210> SEQ ID NO 22
<211> LENGTH: 108
<212> TYPE: PRT
<213> ORGANISM: Homo sapiens

<400> SEQUENCE: 22

```
Ala Thr Gly Val His Ser Asp Ile Val Met Thr Gln Ser Pro Ser Ser
 1               5                  10                  15

Leu Ser Ala Ser Val Gly Asp Arg Val Thr Ile Thr Cys Lys Ala Ser
                20                  25                  30

Gln Asn Val Gly Thr Asn Val Ala Trp Tyr Gln Gln Lys Pro Gly Lys
            35                  40                  45

Ala Pro Lys Ala Leu Ile Tyr Ser Ala Ser Tyr Arg Tyr Ser Gly Val
        50                  55                  60

Pro Asp Arg Phe Ser Gly Ser Gly Ser Gly Thr Asp Phe Thr Leu Thr
 65              70                  75                  80

Ile Ser Ser Leu Gln Pro Glu Asp Ile Ala Thr Tyr Tyr Cys Gln Gln
                 85                  90                  95

Tyr Asn Ser Tyr Pro Leu Thr Phe Gly Gly Gly Thr
                100                 105
```

<210> SEQ ID NO 23
<211> LENGTH: 90
<212> TYPE: PRT
<213> ORGANISM: Artificial Sequence
<220> FEATURE:
<223> OTHER INFORMATION: Derivative of human light chain REI, REI-con

<400> SEQUENCE: 23

```
Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ile Lys Tyr
                20                  25                  30

Leu Asn Trp Tyr Gln Gln Lys Pro Gly Lys Ala Pro Lys Leu Leu Ile
            35                  40                  45

Tyr Glu Ala Ser Asn Leu Gln Ala Gly Val Pro Ser Arg Phe Ser Gly
        50                  55                  60

Ser Gly Ser Gly Thr Asp Phe Thr Phe Thr Ile Ser Ser Leu Gln Pro
 65              70                  75                  80

Glu Asp Ile Ala Thr Tyr Tyr Cys Gln Gln
                 85                  90
```

ERYTHROPOIETIN RECEPTOR ANTIBODIES

CROSS REFERENCE TO RELATED APPLICATIONS

This application is a §371 of International Application Number PCT/US00/10284, filed 14 Apr. 2000, which claims the benefit of U.S. Provisional Application No. 60/129,263, filed 14 Apr. 1999.

The entire contents of each of the foregoing applications are incorporated herein by reference.

FIELD OF THE INVENTION

This invention relates to agonist monoclonal antibodies (mAb) that bind to the erythropoietin receptor (EpoR) and to the use of such antibodies for therapeutic purposes. This invention also relates to antagonist monoclonal antibodies (mAb) that bind to the erythropoietin receptor (EpoR) and to the use of such antibodies for therapeutic purposes.

BACKGROUND OF THE INVENTION

Erythropoietin (Epo) is the naturally occurring hematopoietic growth factor required for the production of mature red blood cells. Epo has a molecular mass of 18.4 kD excluding carbohydrate, and when naturally glycosylated is 35 kD (Roberts, D. and Smith, D. J., *J. Mol. Endocrinology* 12, 131, 1994). The protein is encoded by only one gene (Youssoufian, H., Zon, L. I., Orkin, S. H., D'Andrea, A. D. & Lodish, H. F. *Mol. Cell. Biol.* 10, 3675–3682 (1990), Maouche, L., et al. *Blood* 78, 2557–2563 (1991). This growth factor stimulates the proliferation of early and late erythroid specific progenitor cells as well as the hemoglobination of proerythroblasts and their differentiation into mature red blood cells.

Recombinant human Epo (rEpo) has an established market and is routinely used in the care of patients with renal failure, where kidney damage results in anemia due to insufficient production of Epo (Foa, P. *Acta Haematol* 86, 162–168 (1991)). Furthermore, Epo has also been shown to be useful in specific clinical settings, such as autologous blood transfusion prior to elective surgery, prevention and/or treatment of anemia induced by cytoreductive drugs, and for the treatment of anemia patients receiving zidovudine for HIV infection (Ascensao, J. A., Bilgrami, S. & Zanjani, E. D. *Am. J. Pediat. Hematol.* 13, 376–387 (1991)). Therapy with rEpo is remarkably well tolerated by most patients with few, if any, major adverse reactions reported. Despite the success of rEpo in the clinic, its full potential has not been realized due to limitations imposed by the short half life of rEpo that require frequent dosing and the high cost of treatment. The current recommended dosing is 3× a week delivered subcutaneously.

Epo is a member of a family of structurally and genetically related ligands, which include IL-2, IL-3, IL4, IL-5, IL-6, IL-7, IL-10, IL-12, IL-13, LIF, G-CSF, GM-CSF, M-CSF, Epo, growth hormone and PRL (see Young, P. R. *Curr. Opin. Biotech.* 3, 408, (1992) for review). The structures of several of the ligands have been determined by X-ray crystallography and/or NMR, and all have a basic core structure of a four α-helical bundle with an up—up—down—down connectivity. A similar fold is predicted for other members of the family based on modeling and gene structure.

Epo acts through a cell surface receptor which belongs to the hematopoietic cytokine receptor family. EpoR has been cloned from mouse and human and exists in both membrane-bound and secreted forms (D'Andrea, A. D., Lodish, H. F. & Wong, G. G. *Cell* 57, 277–285 (1989), Jones, S. S., D'Andrea, A. D., Haines, L. L. & Wong, G. G. *Blood* 76, 31–35 (1990), Nakamura, Y., Komatsu, N. & Nakauichi, H. *Science* 257, 1138–1141 (1992) and Todokoro, K., Kuramochi, T., Nagasawa, T., Abe, T. & Ikawa, Y. *Gene* 106, 283–284 (1991)). The extracellular domain of the receptors contains the "hematopoietic motif" which consists of two 100 amino acid long fibronectin-like domains and a conserved WSXWS sequence motif, while the intracellular domains contain several conserved regions but do not encode an endogenous kinase activity. Examination of the growth hormone ligand-receptor complex structure (De Vos, A. M., Ultsch, M. & Kossiakoff, A. A. *Science* 255, 306, (1992)) and extensive mutagenesis of the ligands (reviewed in Young, P. R., supra,) suggests that, in general, the interaction between receptor and ligand is similar for all members of the hematopoietic cytokine family, with the loops of the two fibronectin domains of each receptor subunit interacting with the amino and carboxy-terminal α-helices.

All ligands in this family stimulate biological activity by causing the aggregation of single or multiple receptor subunits in target cells. In the case of Epo, the critical event appears to be the dimerization of a single receptor subunit. Mutant cloned receptors which lead to constitutively active, ligand-independent growth in transfected cell lines, are constitutively dimeric (Watowich, S. S., et al. *Proc. Natl. Acad. Sci. USA* 89, 2140, (1992)). Furthermore, in vitro studies of complex formation between Epo and the extracellular domain of EpoR suggest a 1:2 ligand:receptor interaction (Harris, K. W., Mitchell, R. A. & Winkelmann, J. C. *J. Biol. Chem.* 267, 15205, (1992), Philo, J. S., Aoki, K. H., Arakawa, T., Narhi, L. O. & Wen, J. *Biochemistry* 35, 1681, (1996)). More recently a peptide with Epo minimetic activity was shown to dimerize the receptor (Wrighton, N. C. et al., *Science* 273, 458–463 (1996)).

The interaction of Epo with its receptor initiates a chain of events involving tyrosine and serine-threonine protein kinases which culminate in changes in the pattern of cellular gene expression, proliferation and differentiation. While there have been many advances in the understanding of the signal transduction pathways following Epo binding to its receptor (for a review see: Ihle, J. N. *Nature* 377, 591–594 (1995)), it is still not clear how progenitor cells decide between proliferation and differentiation.

The finding that dimerization of the receptor is a key step in the stimulation of mitogenesis by Epo suggests another approach to novel Epo-like agonists. In at least three examples of other receptors where homodimerization is induced by receptor binding, monoclonal antibodies have been developed which also had agonist properties. These include monoclonal antibodies to EGF, TNF and growth hormone receptors (Schreiber, A. B., Libermann, T. A., Lax, I., Yarden, Y. & Schlessinger, J. *J. Biol. Chem.* 258, 846–853 (1983), Defize, L. H. K., Moolenaar, W. H., van der Saag, P. T. & de Laat, S. W. *EMBO J.* 5, 1187–1192 (1986), Engelmann, H., et al. *J. Biol. Chem.* 265, 14497–14504 (1990), Fuh, G., et al. *Science* 256, 1677–1680 (1992)). In all three cases, the monoclonal antibody, by virtue of its two antigen recognition sites, was able to bring together two receptors and activate them. Fab fragments made from these mAbs were inactive. In some cases, the apparent affinity of the antibody for receptor was comparable to that of the ligand (e.g., growth hormone, Fuh, G., et al. *Science* 256, 1677–1680 (1992)). More recently, there were reports of monoclonal antibodies raised to the Epo receptor that have Epo-like activity (Schneider. H. et al., *Blood* 89, 473482 (1997) and Elliot, E. Et al., *J. Biol. Chem.* 271, 24691–24697 (1996)). However, these reports indicated that the frequency of obtaining agonist monoclonal antibodies to the Epo receptor was very low, and their potency was low and hence unsuitable for use therapeutically.

Clearly, there is a need to develop high affinity, potent agonist antibodies to the EpoR which will have sufficient activity to work in vivo at therapeutically acceptable concentrations.

There are available well known methods for humanization of non-human mAbs that result in less immunogenic antibodies for human therapy, yet retain full binding avidity. These methods can be applied to receptor agonist mAbs whose mode of action is the dimerization of receptors in a manner that mimics the action of the natural receptor ligand.

A humanized agonist mAb with equal or better affinity than rEpo for its receptor and an appropriate Fc region would be expected to have a longer in vivo half-life. This would be expected to produce an Epo-like protein with a lower frequency of dosing compared to rEpo, which is presently given three times a week by subcutaneous injection.

SUMMARY OF THE INVENTION

One aspect of the present invention is a method for enhancing erythropoiesis in a animal comprising administering an effective dose of an erythropoietin receptor agonist antibody having the identifying characteristics of monoclonal antibody 3G9; 1-0 IgG1,1-0k; 1-0 IgG4PE,1-0k; S14 IgG4PE,1-0k; 1-0 IgG1,REIk; 1-0 IgG4PE,REIk; 1-0 IgG 1,5-0k; 1-0 IgG4PE,5-0k, 1-0 IgG1,6-0k; or 1-0 IgG4PE,6-0k.

Another aspect of the invention is an EpoR agonist antibody having the identifying characteristics of monoclonal antibody 3G9; 1-0 IgG1,1-0k; 1-0 IgG4PE,1-0k; S14 IgG4PE,1-0k; 1-0 IgG1,REIk; 1-0 IgG4PE,REIk; 1-0 IgG1, 5-0k; 1-0 IgG4PE,5-0k, 1-0 IgG1,6-0k; or 1-0 IgG4PE,6-0k.

Another aspect of the invention is a hybridoma having the identifying characteristics of cell line 3G9.

Yet another aspect of the invention is an EpoR agonist antibody comprising a $V_H$ amino acid sequence as set forth in SEQ ID NO: 2 and a $V_L$ amino acid sequence as set forth in SEQ ID NO: 4.

Yet another aspect of the invention is an EpoR agonist antibody comprising a $V_H$ amino acid sequence as set forth in SEQ ID NO: 12 and a $V_L$ amino acid sequence as set forth in SEQ ID NO: 16.

Yet another aspect of the invention is an EpoR agonist antibody comprising a $V_H$ amino acid sequence as set forth in SEQ ID NO: 14 and a $V_L$ amino acid sequence as set forth in SEQ ID NO: 16.

Yet another aspect of the invention is an EpoR agonist antibody comprising a $V_H$ amino acid sequence as set forth in SEQ ID NO: 12 and a $V_L$ amino acid sequence as set forth in SEQ ID NO: 18.

Yet another aspect of the invention is an EpoR agonist antibody comprising a $V_H$ amino acid sequence as set forth in SEQ ID NO: 12 and a $V_L$ amino acid sequence as set forth in SEQ ID NO: 20.

Yet another aspect of the invention is an EpoR agonist antibody comprising a $V_H$ amino acid sequence as set forth in SEQ ID NO: 12 and a $V_L$ amino acid sequence as set forth in SEQ ID NO: 22.

Yet another aspect of the invention is an EpoR agonist antibody comprising a $V_H$ amino acid sequence selected from the group consisting of SEQ ID NOs: 2, 12 or 14.

Yet another aspect of the invention is an EpoR agonist antibody comprising a $V_L$ amino acid sequence selected from the group consisting of SEQ ID NOs: 4, 16, 18, 20 or 22.

Yet another aspect of the invention is an immunoglobulin heavy chain complementarity determining region, the amino acid sequence of which is selected from the group consisting of SEQ ID NOs: 5, 6 and 7.

Yet another aspect of the invention is an immunoglobulin light chain complementarity determining region, the amino acid sequence of which is selected from the group consisting of SEQ ID NOs: 8, 9 and 10.

Yet another aspect of the invention is an isolated nucleic acid molecule encoding the amino acid sequence of SEQ ID NOs: 2, 4, 12, 14, 16, 18, 20 or 22 and functional fragments or analogs therof.

DETAILED DESCRIPTION OF THE INVENTION

Figure 1:
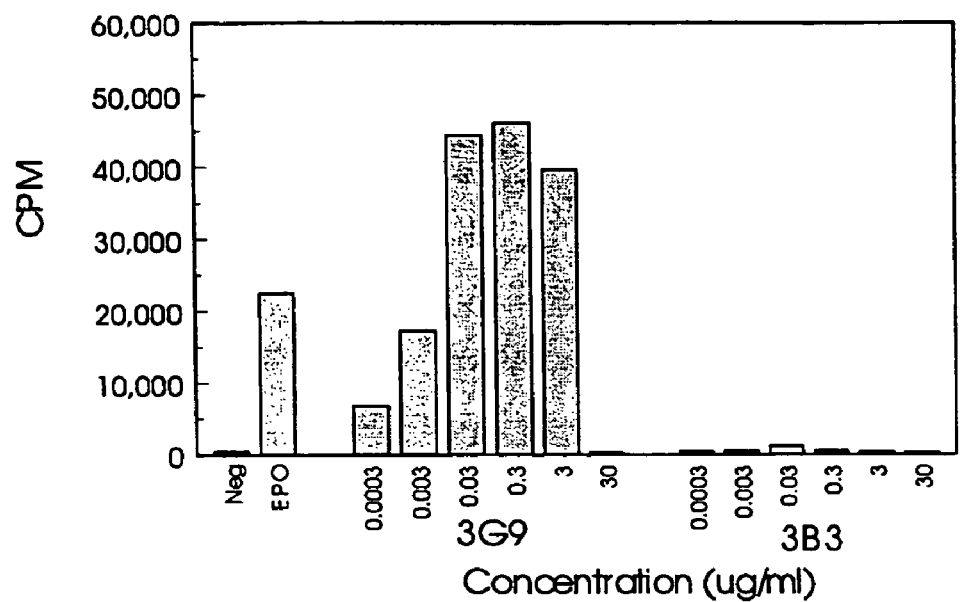
FIG. 1 is a graph of experimental results demonstrating the activity of monoclonal antibodies 3G9 and 3B3 in the UT7-Epo cell proliferation assay.

All publications, including but not limited to patents and patent applications, cited in this specification are herein incorporated by reference as though fully set forth.

As used herein, the term "enhancing erythropoiesis" and "erythropoietic" means increasing the production of erythrocytes as well as increasing the production of precursors and components of erythrocytes.

As used herein, the term "decreasing erythropoiesis" and derivatives thereof means decreasing the production of erythrocytes as well as decreasing the production of precursors and components of erythrocytes.

As used herein, the term "agonist activity" refers to the activity of an antibody that binds to human EpoR and enhances erythropoiesis.

As used herein, the term "antagonist activity" refers to the activity of an antibody that binds to human EpoR and decreases erythropoiesis.

As used herein, the term "treating" and derivatives thereof means prophylactic or therapeutic therapy.

The present invention provides a variety of antibodies, including altered antibodies and fragments thereof directed against EpoR, which are characterized by agonist activity (and by antagonist activity). Exemplary anti-EpoR agonist antibodies are the murine monoclonal antibody 3G9 and humanized derivatives 1-0 IgG1,1-0k; 1-0-0 IgG4PE,1-0k; S14 IgG4PE,1-0k; 1-0 IgG1,REIk; 1-0 IgG4PE,REIk; 1-0 IgG1,5-0k; 1-0 IgG4PE,5-0k; 1-0 IgG1,6-0k; and 1-0 IgG4PE,6-0k.

"Antibodies" refers to immunoglobulins which can be prepared by conventional hybridoma techniques, phage display combinatorial libraries, immunoglobulin chain shuffling and humanization techniques. Also included are fully human monoclonal antibodies. As used herein, "antibody" also includes "altered antibody" which refers to a protein encoded by an altered immunoglobulin coding region, which may be obtained by expression in a selected host cell. Such altered antibodies are engineered antibodies (e.g., chimeric or humanized antibodies) or antibody fragments lacking all or part of an immunoglobulin constant region, e.g., Fv, Fab, Fab' or F(ab')$_2$ and the like. These antibody products are useful in therapeutic and pharmaceutical compositions for treating anemias, cytopenias, acute renal failure and other conditions with depressed erythrocyte production.

"Altered immunoglobulin coding region" refers to a nucleic acid sequence encoding an altered antibody of the invention. When the altered antibody is a complementarity determining region-grafted (CDR-grafted) or humanized antibody, the sequences that encode the CDRs from a non-human immunoglobulin are inserted into a first immunoglobulin partner comprising human variable framework sequences. Optionally, the first immunoglobulin partner is operatively linked to a second immunoglobulin partner.

"First immunoglobulin partner" refers to a nucleic acid sequence encoding a human framework or human immunoglobulin variable region in which the native (or naturally-occurring) CDR-encoding regions are replaced by the CDR-encoding regions of a donor antibody. The human variable region can be an immunoglobulin heavy chain, a light chain (or both chains), an analog or functional fragments thereof. Such CDR regions, located within the variable region of antibodies (immunoglobulins) can be determined by known methods in the art. For example Kabat et al. in "Sequences of Proteins of Immunological Interest", 4th Ed., U.S. Department of Health and Human Services, National Institutes of Health (1987) disclose rules for locating CDRs. In addition, computer programs are known which are useful for identifying CDR regions/structures.

"Second immunoglobulin partner" refers to another nucleotide sequence encoding a protein or peptide to which the first immunoglobulin partner is fused in frame or by means of an optional conventional linker sequence (i.e., operatively linked). Preferably, it is an immunoglobulin gene. The second immunoglobulin partner may include a nucleic acid sequence encoding the entire constant region for the same (i.e., homologous, where the first and second altered antibodies are derived from the same source) or an additional (i.e., heterologous) antibody of interest. It may be an immunoglobulin heavy chain or light chain (or both chains as part of a single polypeptide). The second immunoglobulin partner is not limited to a particular immunoglobulin class or isotype. In addition, the second immunoglobulin partner may comprise part of an immunoglobulin constant region, such as found in a Fab, or F(ab)$_2$ (i.e., a discrete part of an appropriate human constant region or framework region). Such second immunoglobulin partner may also comprise a sequence encoding an integral membrane protein exposed on the outer surface of a host cell, e.g., as part of a phage display library, or a sequence encoding a protein for analytical or diagnostic detection, e.g., horseradish peroxidase, β-galactosidase, etc.

The terms Fv, Fc, Fd, Fab, Fab' or F(ab')$_2$ are used with their standard meanings. See, e.g., Harlow et al. in "Antibodies A Laboratory Manual", Cold Spring Harbor Laboratory, (1988).

As used herein, an "engineered antibody" describes a type of altered antibody, i.e., a full-length synthetic antibody (e.g., a chimeric or humanized antibody as opposed to an antibody fragment) in which a portion of the light and/or heavy chain variable domains of a selected acceptor antibody are replaced by analogous parts from one or more donor antibodies which have specificity for the selected epitope. For example, such molecules may include antibodies characterized by a humanized heavy chain associated with an unmodified light chain (or chimeric light chain), or vice versa. Engineered antibodies may also be characterized by alteration of the nucleic acid sequences encoding the acceptor antibody light and/or heavy variable domain framework regions in order to retain donor antibody binding specificity. These antibodies can comprise replacement of one or more CDRs (preferably all) from the acceptor antibody with CDRs from a donor antibody described herein.

A "chimeric antibody" refers to a type of engineered antibody which contains a naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one or more human immunoglobulins. In addition, framework support residues may be altered to preserve binding affinity. See, e.g., Queen et al., *Proc. Natl. Acad Sci USA,* 86, 10029–10032 (1989), Hodgson et al., *Bio/Technology* 9, 421 (1991). Furthermore, as decribed herein, additional residues may be altered to preserve the agonist activity of the donor antibody.

The term "donor antibody" refers to a monoclonal or recombinant antibody which contributes the nucleic acid sequences of its variable regions, CDRs or other functional fragments or analogs thereof to a first immunoglobulin partner, so as to provide the altered immunoglobulin coding region and resulting expressed altered antibody with the antigenic specificity and neutralizing activity characteristic of the donor antibody. One donor antibody suitable for use in this invention is a murine agonist monoclonal antibody designated as 3G9.

The term "acceptor antibody" refers to monoclonal or recombinant antibodies heterologous to the donor antibody, which contributes all, or a portion, of the nucleic acid sequences encoding its heavy and/or light chain framework regions and/or its heavy and/or light chain constant regions or V region subfamily consensus sequences to the first immunoglobulin partner. Preferably, a human antibody is the acceptor antibody.

"CDRs" are defined as the complementarity determining region amino acid sequences of an antibody which are the hypervariable regions of immunoglobulin heavy and light chains. See, e.g., Kabat et al., *Sequences of Proteins of Immunological Interest*, 4th Ed., U.S. Department of Health and Human Services, National Institutes of Health (1987). There are three heavy chain and three light chain CDRs or CDR regions in the variable portion of an immunoglobulin. Thus, "CDRs" as used herein refers to all three heavy chain CDRs, or all three light chain CDRs or both all heavy and all light chain CDRs, if appropriate.

CDRs provide the majority of contact residues for the binding of the antibody to the antigen or epitope. CDRs of interest in this invention are derived from donor antibody variable heavy and light chain sequences, and include analogs of the naturally occurring CDRs, which analogs share or retain the same antigen binding specificity and/or agonist ability as the donor antibody from which they were derived, yet may exhibit increased affinity for the antigen. An exemplary process for obtaining analogs is affinity maturation by means of phage display technology as reviewed by Hoogenboom, *Trends in Biotechnology* 15, 62–70 (1997); Barbas et al., *Trends in Biotechnology* 14, 230–234 (1996); and Winter et al., *Ann. Rev. Immunol.* 12, 433–455 (1994) and described by Irving et al., *Immunotechnology* 2, 127–143 (1996).

By "sharing the antigen binding specificity or agonist ability" is meant, for example, that although mAb 3G9 may be characterized by a certain level of agonist activity, a CDR encoded by a nucleic acid sequence of 3G9 in an appropriate structural environment may have a lower or higher activity. It is expected that CDRs of 3G9 in such environments will nevertheless recognize the same epitope(s) as 3G9.

A "functional fragment" is a partial heavy or light chain variable sequence (e.g., minor deletions at the amino or carboxy terminus of the immunoglobulin variable region) which retains the same antigen binding specificity and/or agonist ability as the antibody from which the fragment was derived.

An "analog" is an amino acid sequence modified by at least one amino acid, wherein said modification can be chemical or a substitution or a rearrangement of a few amino acids (i.e., no more than 10) and corresponding nucleic acid sequences, which modification permits the amino acid sequence to retain the biological characteristics, e.g., antigen specificity and high affinity, of the unmodified sequence. Exemplary nucleic acid analogs include silent mutations which can be constructed, via substitutions, to create certain endonuclease restriction sites within or surrounding CDR-encoding regions.

Analogs may also arise as allelic variations. An "allelic variation or modification" is an alteration in the nucleic acid sequence encoding the amino acid or peptide sequences of the invention. Such variations or modifications may be due to degeneracy in the genetic code or may be deliberately engineered to provide desired characteristics. These variations or modifications may or may not result in alterations in any encoded amino acid sequence.

The term "effector agents" refers to non-protein carrier molecules to which the altered antibodies, and/or natural or synthetic light or heavy chains of the donor antibody or other fragments of the donor antibody may be associated by conventional means. Such non-protein carriers can include conventional carriers used in the diagnostic field, e.g., polystyrene or other plastic beads, polysaccharides, e.g., as used in the BIAcore (Pharmacia) system, or other non-protein substances useful in the medical field and safe for administration to humans and animals. Other effector agents may include a macrocycle, for chelating a heavy metal atom or radioisotopes. Such effector agents may also be useful to increase the half-life of the altered antibodies, e.g., polyethylene glycol.

For use in constructing the antibodies, altered antibodies and fragments of this invention, a non-human species such as bovine, ovine, monkey, chicken, rodent (e.g., murine and rat) may be employed to generate a desirable immunoglobulin upon presentment with human EpoR or a peptide epitope therefrom. Conventional hybridoma techniques are employed to provide a hybridoma cell line secreting a non-human mAb to the EpoR. Such hybridomas are then screened for binding and agonist activity as described in the Examples section. Alternatively, fully human mAbs can be generated by techniques known to those skilled in the art and used in this invention.

An exemplary agonist mAb of the present invention is mAb 3G9, a murine antibody which can be used for the development of a chimeric or humanized molecule. The 3G9 mAb is characterized by agonist activity on erythrocyte production as measured by the CFU-E assay and is produced by the hybridoma cell line 3G9. Other exemplary agonist mAbs are disclosed in U.S. patent application Ser. No. 08/960,733.

The present invention also includes the use of Fab fragments or F(ab')$_2$ fragments derived from mAbs directed against human EpoR as bivalent fragments. These fragments are useful as agents having agonist activity at the human EpoR. A Fab fragment contains the entire light chain and amino terminal portion of the heavy chain. An F(ab')$_2$ fragment is the fragment formed by two Fab fragments bound by disulfide bonds. The mAbs 3G9 and other similar high affinity antibodies provide sources of Fab fragments and F(ab')$_2$ fragments which can be obtained by conventional means, e.g., cleavage of the mAb with the appropriate proteolytic enzymes, papain and/or pepsin, or by recombinant methods. These Fab and F(ab')$_2$ fragments are useful themselves as therapeutic, prophylactic or diagnostic agents, and as donors of sequences including the variable regions and CDR sequences useful in the formation of recombinant or humanized antibodies as described herein.

The Fab and F(ab')$_2$ fragments can be constructed via a combinatorial phage library (see, e.g., Winter et al., *Ann. Rev. Immunol.*, 12:433455 (1994)) or via immunoglobulin chain shuffling (see, e.g., Marks et al., *Bio/Technology*, 10:779–783 (1992)), wherein the Fd or $V_H$ immunoglobulin from a selected antibody (e.g., 3G9) is allowed to associate with a repertoire of light chain immunoglobulins, $V_L$ (or $V_K$), to form novel Fabs. Conversely, the light chain immunoglobulin from a selected antibody may be allowed to associate with a repertoire of heavy chain immunoglobulins, $V_H$ (or Fd), to form novel Fabs. EpoR agonist Fabs can be obtained by allowing the Fd of mAb 3G9 to associate with a repertoire of light chain immunoglobulins. Hence, one is able to recover neutralizing Fabs with unique sequences (nucleotide and amino acid) from the chain shuffling technique.

The mAb 3G9 or other antibodies described above may contribute sequences, such as variable heavy and/or light chain peptide sequences, framework sequences, CDR sequences, functional fragments, and analogs thereof, and the nucleic acid sequences encoding them, useful in designing and obtaining various altered antibodies which are characterized by the antigen binding specificity of the donor antibody.

The nucleic acid sequences of this invention, or fragments thereof, encoding the variable light chain and heavy chain peptide sequences are also useful for mutagenic introduction of specific changes within the nucleic acid sequences encoding the CDRs or framework regions, and for incorporation of the resulting modified or fusion nucleic acid sequence into a plasmid for expression. For example, silent substitutions in the nucleotide sequence of the framework and CDR-encoding regions can be used to create restriction enzyme sites which facilitate insertion of mutagenized CDR and/or framework regions. These CDR-encoding regions can be used in the construction of the humanized antibodies of the invention.

The nucleic and amino acid sequences of the 3G9 heavy chain variable region is listed in SEQ ID NO: 1. The CDR amino acid sequences from this region are listed in SEQ ID Nos: 5, 6 and 7.

The nucleic and amino acid sequences of the 3G9 light chain variable region listed in SEQ ID NO: 3. The CDR amino acid sequences from this region are listed in SEQ ID Nos: 8, 9 and 10.

Taking into account the degeneracy of the genetic code, various coding sequences may be constructed which encode the variable heavy and light chain amino acid sequences and CDR sequences of the invention as well as functional fragments and analogs thereof which share the antigen specificity of the donor antibody. The isolated nucleic acid sequences of this invention, or fragments thereof, encoding the variable chain peptide sequences or CDRs can be used to produce altered antibodies, e.g., chimeric or humanized antibodies or other engineered antibodies of this invention when operatively combined with a second immunoglobulin partner.

It should be noted that in addition to isolated nucleic acid sequences encoding portions of the altered antibody and antibodies described herein, other such nucleic acid sequences are encompassed by the present invention, such as those complementary to the native CDR-encoding sequences or complementary to the modified human framework regions surrounding the CDR-encoding regions. Useful DNA sequences include those sequences which hybridize under stringent hybridization conditions to the DNA sequences. See, T. Maniatis et al., *Molecular Cloning: A Laboratory Manual*, Cold Spring Harbor Laboratory (1982), pp. 387–389. An example of one such stringent hybridization condition is hybridization at 4×SSC at 65° C., followed by a washing in 0.1×SSC at 65° C. for one hour. Alternatively, an exemplary stringent hybridization condition is 50% formamide, 4×SSC at 42° C. Preferably, these hybridizing DNA sequences are at least about 18 nucleotides in length, i.e., about the size of a CDR.

Altered immunoglobulin molecules can encode altered antibodies which include engineered antibodies such as chimeric antibodies and humanized antibodies. A desired altered immunoglobulin coding region contains CDR-encoding regions that encode peptides having the antigen specificity of an EpoR antibody, preferably a high-affinity agonist antibody such as provided by the present invention, inserted into a first immunoglobulin partner such as a human framework or human immunoglobulin variable region.

Preferably, the first immunoglobulin partner is operatively linked to a second immunoglobulin partner. The second immunoglobulin partner is defined above, and may include a sequence encoding a second antibody region of interest, for example an Fc region. Second immunoglobulin partners may also include sequences encoding another immunoglobulin to which the light or heavy chain constant region is fused in frame or by means of a linker sequence. Engineered antibodies directed against functional fragments or analogs of the EpoR may be designed to elicit enhanced binding with the same antibody.

The second immunoglobulin partner may also be associated with effector agents as defined above, including non-protein carrier molecules, to which the second immunoglobulin partner may be operatively linked by conventional means.

Fusion or linkage between the second immunoglobulin partners, e.g., antibody sequences, and the effector agent may be by any suitable means, e.g., by conventional covalent or ionic bonds, protein fusions, or hetero-bifunctional cross-linkers, e.g., carbodiimide, glutaraldehyde and the like. Such techniques are known in the art and are described in conventional chemistry and biochemistry texts.

Additionally, conventional linker sequences which simply provide for a desired amount of space between the second immunoglobulin partner and the effector agent may also be constructed into the altered immunoglobulin coding region. The design of such linkers is well known to those of skill in the art.

In addition, signal sequences for the molecules of the invention may be modified by techniques known to those skilled in the art to enhance expression.

A preferred altered antibody contains a variable heavy and/or light chain peptide or protein sequence having the antigen specificity of mAb 3G9, e.g., the $V_H$ and $V_L$ chains. Still another desirable altered antibody of this invention is characterized by the amino acid sequence containing at least one, and preferably all of the CDRs of the variable region of the heavy and/or light chains of the murine antibody molecule 3G9 with the remaining sequences being derived from a human source, or a functional fragment or analog thereof.

In a further embodiment, the altered antibody of the invention may have attached to it an additional agent. For example, recombinant DNA technology may be used to produce an altered antibody of the invention in which the Fc fragment or CH2 CH3 domain of a complete antibody molecule has been replaced by an enzyme or other detectable molecule (i.e., a polypeptide effector or reporter molecule) provided that the dimeric characteristic of the complete antibody molecule is retained.

The second immunoglobulin partner may also be operatively linked to a non-immunoglobulin peptide, protein or fragment thereof heterologous to the CDR-containing sequence having antigen specificity to the EpoR. The resulting protein may exhibit both antigen specificity and characteristics of the non-immunoglobulin upon expression. That fusion partner characteristic may be, e.g., a functional characteristic such as another binding or receptor domain or a therapeutic characteristic if the fusion partner is itself a therapeutic protein or additional antigenic characteristics.

Another desirable protein of this invention may comprise a complete antibody molecule, having full length heavy and light chains or any discrete fragment thereof, such as the Fab or F(ab')$_2$ fragments, a heavy chain dimer or any minimal recombinant fragments thereof such as an F$_V$ or a single-chain antibody (SCA) or any other molecule with the same specificity as the selected donor mAb, e.g., the 3G9 mAb. Such protein may be used in the form of an altered antibody or may be used in its unfused form.

Whenever the second immunoglobulin partner is derived from an antibody different from the donor antibody, e.g., any isotype or class of immunoglobulin framework or constant regions, an engineered antibody results. Engineered antibodies can comprise immunoglobulin constant regions and variable framework regions from one source, e.g., the acceptor antibody, and one or more (preferably all) CDRs from the donor antibody, e.g., the 3G9 mAb. In addition, alterations, e.g., deletions, substitutions, or additions, of the acceptor mAb light and/or heavy variable domain framework region at the nucleic acid or amino acid levels, or the donor CDR regions may be made in order to retain donor antibody antigen binding specificity.

Such engineered antibodies are designed to employ one (or both) of the variable heavy and/or light chains of the EpoR mAb (optionally modified as described) or one or more of the heavy or light chain CDRs. The engineered antibodies of the invention exhibit agonist activity.

Such engineered antibodies may include a humanized antibody containing the framework regions of a selected human immunoglobulin or subtype or a chimeric antibody containing the human heavy and light chain constant regions fused to the EpoR mAb functional fragments. A suitable human (or other animal) acceptor antibody may be one selected from a conventional database, e.g., the KABAT® database, Los Alamos database, and Swiss Protein database, by homology to the nucleotide and amino acid sequences of the donor antibody. A human antibody characterized by a homology to the V region frameworks of the donor antibody or V region subfamily consensus sequences (on an amino acid basis) may be suitable to provide a heavy chain variable framework region for insertion of the donor CDRs. A suitable acceptor antibody capable of donating light chain variable framework regions may be selected in a similar manner. It should be noted that the acceptor antibody heavy and light chains are not required to originate from the same acceptor antibody.

Preferably, the heterologous framework and constant regions are selected from human immunoglobulin classes and isotypes, such as IgG (subtypes 1 through 4), IgM, IgA, and IgE. IgG1, k and IgG4, k are preferred. Particularly preferred is IgG 4, k. Most particularly preferred is the IgG4 subtype variant containing the mutations S228P and L235E (PE mutation) in the heavy chain constant region which results in reduced effector function. This IgG4 subtype variant is known herein as IgG4PE. See U.S. Pat. Nos. 5,624,821 and 5,648,260.

The acceptor antibody need not comprise only human immunoglobulin protein sequences. For instance, a gene may be constructed in which a DNA sequence encoding part of a human immunoglobulin chain is fused to a DNA sequence encoding a non-immunoglobulin amino acid sequence such as a polypeptide effector or reporter molecule.

A particularly preferred humanized antibody contains CDRs of 3G9 mAb inserted onto the framework regions of a selected human antibody sequence. For agonist humanized antibodies, one, two or preferably three CDRs from the 3G9 antibody heavy chain and/or light chain variable regions are inserted into the framework regions of the selected human antibody sequence, replacing the native CDRs of the human antibody.

Preferably, in a humanized antibody, the variable domains in both human heavy and light chains have been engineered by one or more CDR replacements. It is possible to use all six CDRs, or various combinations of less than the six CDRs. Preferably all six CDRs are replaced. It is possible to replace the CDRs only in the human heavy chain, using as light chain the unmodified light chain from the human acceptor antibody. Still alternatively, a compatible light chain may be selected from another human antibody by recourse to conventional antibody databases. The remainder of the engineered antibody may be derived from any suitable acceptor human immunoglobulin.

The engineered humanized antibody thus preferably has the structure of a natural human antibody or a fragment thereof, and possesses the combination of properties required for effective therapeutic use, e.g., treatment of anemias, cytopenias, acute renal failure and other conditions with depressed erythrocyte production in man.

Most preferably, the humanized antibodies have a heavy chain V region (V$_H$) amino acid sequence as set forth in SEQ ID NOs: 12 and 14. Also most preferred are humanized antibodies having a light chain V region (V$_L$) amino acid sequence as set forth in SEQ ID NOs: 16, 18, 20 and 22. Particularly preferred is the humanized antibody 1-0 IgG 1,1-0k comprising a V$_H$ amino acid sequence as set forth in SEQ ID NO: 12 and a V$_L$ amino acid sequence as set forth in SEQ ID NO: 16. Also particularly preferred is the humanized antibody 1-0 IgG4PE, 1-0k comprising a V$_H$ amino acid sequence as set forth in SEQ ID NO: 12 and a V$_L$ amino acid sequence as set forth in SEQ ID NO: 16. Also particularly preferred is the humanized antibody S14 IgG4PE,1-0k comprising a V$_H$ amino acid sequence as set forth in SEQ ID NO: 14 and a V$_L$ amino acid sequence as set forth in SEQ ID NO: 16. Also particularly preferred is the humanized antibody 1-0 IgG1,REIk comprising a V$_H$ amino acid sequence as set forth in SEQ ID NO: 12 and a V$_L$ amino acid sequence as set forth in SEQ ID NO: 18. Also particularly preferred is the humanized antibody 1-0 IgG4PE,REIk comprising a V$_H$ amino acid sequence as set forth in SEQ ID NO: 12 and a V$_L$ amino acid sequence as set forth in SEQ ID NO: 18. Also particularly preferred is the humanized antibody 1-0 IgG1,5-0k comprising a V$_H$ amino acid sequence as set forth in SEQ ID NO: 12 and a V$_L$ amino acid sequence as set forth in SEQ ID NO: 20. Also particularly preferred is the humanized antibody 1-0 IgG4PE,5-0k comprising a V$_H$ amino acid sequence as set forth in SEQ ID NO: 12 and a V$_L$ amino acid sequence as set forth in SEQ ID NO: 20. Also particularly preferred is the humanized antibody 1-0 IgG1,6-0k comprising a V$_H$ amino acid sequence as set forth in SEQ ID NO: 12 and a V$_L$ amino acid sequence as set forth in SEQ ID NO: 22. Also particularly preferred is the humanized antibody 1-0 IgG4PE,6-0k comprising a V$_H$ amino acid sequence as set forth in SEQ ID NO: 12 and a V$_L$ amino acid sequence as set forth in SEQ ID NO: 22.

It will be understood by those skilled in the art that an engineered antibody may be further modified by changes in variable domain amino acids without necessarily affecting the specificity and high affinity of the donor antibody (i.e., an analog). It is anticipated that heavy and light chain amino acids may be substituted by other amino acids either in the variable domain frameworks or CDRs or both. These substitutions could be supplied by the donor antibody or consensus sequences from a particular subgroup.

In addition, the constant region may be altered to enhance or decrease selective properties of the molecules of this invention. For example, dimerization, binding to Fc receptors, or the ability to bind and activate complement (see, e.g., Angal et al., *Mol. Immunol*, 30, 105–108 (1993), Xu et al., *J. Biol. Chem*, 269, 3469–3474 (1994), Winter et al., EP 307434-B).

An altered antibody which is a chimeric antibody differs from the humanized antibodies described above by providing the entire non-human donor antibody heavy chain and light chain variable regions, including framework regions, in association with human immunoglobulin constant regions for both chains. It is anticipated that chimeric antibodies which retain additional non-human sequence relative to humanized antibodies of this invention may elicit a significant erythropoietic response in humans. Such antibodies are useful in the prevention of and for treating anemias, cytopenias, acute renal failure and other conditions with depressed erythrocyte production.

Preferably, the variable light and/or heavy chain sequences and the CDRs of mAb 3G9 or other suitable donor mAbs and their encoding nucleic acid sequences, are utilized in the construction of altered antibodies, preferably humanized antibodies, of this invention, by the following process. The same or similar techniques may also be employed to generate other embodiments of this invention.

A hybridoma producing a selected donor mAb, e.g., the murine antibody 3G9, is conventionally cloned and the DNA of its heavy and light chain variable regions obtained by techniques known to one of skill in the art, e.g., the techniques described in Sambrook et al., *Molecular Cloning: A Laboratory Manual*, 2nd edition, Cold Spring Harbor Laboratory (1989). The variable heavy and light regions of 3G9 containing at least the CDR-encoding regions and those portions of the acceptor mAb light and/or heavy variable domain framework regions required in order to retain donor mAb binding specificity, as well as the remaining immunoglobulin-derived parts of the antibody chain derived from a human immunoglobulin, are obtained using polynucleotide primers and reverse transcriptase. The CDR-encoding regions are identified using a known database and by comparison to other antibodies.

A mouse/human chimeric antibody may then be prepared and assayed for binding ability. Such a chimeric antibody contains the entire non-human donor antibody $V_H$ and $V_L$ regions, in association with human Ig constant regions for both chains.

Homologous framework regions of a heavy chain variable region from a human antibody are identified using computerized databases, e.g., KABAT®, and a human antibody characterized by a homology to the V region frameworks of the donor antibody or V region subfamily consensus sequences (on an amino acid basis) to 3G9 is selected as the acceptor antibody. The sequences of synthetic heavy chain variable regions containing the 3G9 CDR-encoding regions within the human antibody frameworks are designed with optional nucleotide replacements in the framework regions to incorporate restriction sites. This designed sequence is then synthesized using long synthetic oligomers. Alternatively, the designed sequence can be synthesized by overlapping oligonucleotides, amplified by polymerase chain reaction (PCR), and corrected for errors. A suitable light chain variable framework region can be designed in a similar manner.

A humanized antibody may be derived from the chimeric antibody, or preferably, made synthetically by inserting the donor mAb CDR-encoding regions from the heavy and light chains appropriately within the selected heavy and light chain framework. Alternatively, a humanized antibody of the invention may be prepared using standard mutagenesis techniques. Thus, the resulting humanized antibody contains human framework regions and donor mAb CDR-encoding regions. There may be subsequent manipulation of framework residues. The resulting humanized antibody can be expressed in recombinant host cells, e.g., COS, CHO or myeloma cells.

A conventional expression vector or recombinant plasmid is produced by placing these coding sequences for the altered antibody in operative association with conventional regulatory control sequences capable of controlling the replication and expression in, and/or secretion from, a host cell. Regulatory sequences include promoter sequences, e.g., CMV or Rous Sarcoma virus promoter, and signal sequences, which can be derived from other known antibodies. Similarly, a second expression vector can be produced having a DNA sequence which encodes a complementary antibody light or heavy chain. Preferably, this second expression vector is identical to the first except with respect to the coding sequences and selectable markers, in order to ensure, as much as possible, that each polypeptide chain is functionally expressed. Alternatively, the heavy and light chain coding sequences for the altered antibody may reside on a single vector.

A selected host cell is co-transfected by conventional techniques with both the first and second vectors (or simply transfected by a single vector) to create the transfected host cell of the invention comprising both the recombinant or synthetic light and heavy chains. The transfected cell is then cultured by conventional techniques to produce the engineered antibody of the invention. The humanized antibody which includes the association of both the recombinant heavy chain and/or light chain is screened from culture by an appropriate assay such as ELISA or RIA. Similar conventional techniques may be employed to construct other altered antibodies and molecules of this invention.

Suitable vectors for the cloning and subcloning steps employed in the methods and construction of the compositions of this invention may be selected by one of skill in the art. For example, the pUC series of cloning vectors, such as pUC19, which is commercially available from supply houses, such as Amersham or Pharmacia, may be used. Additionally, any vector which is capable of replicating readily, has an abundance of cloning sites and selectable genes (e.g., antibiotic resistance) and is easily manipulated may be used for cloning. Thus, the selection of the cloning vector is not a limiting factor in this invention.

Similarly, the vectors employed for expression of the engineered antibodies according to this invention may be selected by one of skill in the art from any conventional vector. The vectors also contain selected regulatory sequences (such as CMV or Rous Sarcoma virus promoters) which direct the replication and expression of heterologous DNA sequences in selected host cells. These vectors contain the above-described DNA sequences which code for the engineered antibody or altered immunoglobulin coding region. In addition, the vectors may incorporate the selected immunoglobulin sequences modified by the insertion of desirable restriction sites for ready manipulation.

The expression vectors may also be characterized by genes suitable for amplifying expression of the heterologous DNA sequences, e.g., the mammalian dihydrofolate reductase gene (DHFR). Other preferable vector sequences include a poly A signal sequence, such as from bovine growth hormone (BGH) and the betaglobin promoter sequence (betaglopro). The expression vectors useful herein may be synthesized by techniques well known to those skilled in this art.

The components of such vectors, e.g., replicons, selection genes, enhancers, promoters, signal sequences and the like, may be obtained from commercial or natural sources or synthesized by known procedures for use in directing the expression and/or secretion of the product of the recombinant DNA in a selected host. Other appropriate expression vectors of which numerous types are known in the art for mammalian, bacterial, insect, yeast and fungal expression may also be selected for this purpose.

The present invention also encompasses a cell line transfected with a recombinant plasmid containing the coding sequences of the engineered antibodies or altered immunoglobulin molecules thereof. Host cells useful for the cloning and other manipulations of these cloning vectors are also conventional. However, most desirably, cells from various strains of *E. coli* are used for replication of the cloning vectors and other steps in the construction of altered antibodies of this invention.

Suitable host cells or cell lines for the expression of the engineered antibody or altered antibody of the invention are preferably mammalian cells such as CHO, COS, a fibroblast cell (e.g., 3T3) and myeloid cells, and more preferably a CHO or a myeloid cell. Human cells may be used, thus enabling the molecule to be modified with human glycosylation patterns. Alternatively, other eukaryotic cell lines may be employed. The selection of suitable mammalian host cells and methods for transformation, culture, amplification, screening and product production and purification are known in the art. See, e.g., Sambrook et al., supra.

Bacterial cells may prove useful as host cells suitable for the expression of the recombinant Fabs of the present invention (see, e.g., Plückthun, A., *Immunol. Rev.*, 130, 151–188 (1992)). However, due to the tendency of proteins expressed in bacterial cells to be in an unfolded or improperly folded form or in a non-glycosylated form, any recombinant Fab produced in a bacterial cell would have to be screened for retention of antigen binding ability. If the molecule expressed by the bacterial cell was produced in a properly folded form, that bacterial cell would be a desirable host. For example, various strains of *E. coli* used for expression are well-known as host cells in the field of biotechnology. Various strains of *B. subtilis, Streptomyces,* other bacilli and the like may also be employed.

Where desired, strains of yeast cells known to those skilled in the art are also available as host cells, as well as insect cells, e.g. *Drosophila* and *Lepidoptera*, and viral expression systems. See, e.g. Miller et al., *Genetic Engineering*, 8, 277–298, Plenum Press (1986) and references cited therein.

The general methods by which the vectors of the invention may be constructed, the transfection methods required to produce the host cells of the invention, and culture methods necessary to produce the altered antibody of the invention from such host cell are all conventional techniques. Likewise, once produced, the altered antibodies of the invention may be purified from the cell culture contents according to standard procedures of the art, including ammonium sulfate precipitation, affinity columns, column chromatography, gel electrophoresis and the like. Such techniques are within the skill of the art and do not limit this invention.

Yet another method of expression of the humanized antibodies may utilize expression in a transgenic animal, such as described in U.S. Pat. No. 4,873,316. This relates to an expression system using the animal's casein promoter which when transgenically incorporated into a mammal permits the female to produce the desired recombinant protein in its milk.

Once expressed by the desired method, the engineered antibody is then examined for in vitro activity by use of an appropriate assay. Presently, conventional ELISA assay formats as well as surface plasmon resonance and isothermal calorimetry are employed to assess qualitative and quantitative binding of the engineered antibody to EpoR. Additionally, other in vitro assays such as CFU-E may also be used to determine agonist activity prior to subsequent human clinical studies performed to evaluate the persistence of the engineered antibody in the body despite the usual clearance mechanisms.

Following the procedures described for humanized antibodies prepared from 3G9, one of skill in the art may also construct humanized antibodies from other donor antibodies, variable region sequences and CDR peptides described herein. Engineered antibodies can be produced with variable region frameworks potentially recognized as "self" by recipients of the engineered antibody. Modifications to the variable region frameworks can be implemented to effect increases in antigen binding and agonist activity without appreciable increased immunogenicity for the recipient. Such engineered antibodies may effectively treat a human for anemias, cytopenias and other conditions with depressed erythrocyte production. Such antibodies may also be useful in the diagnosis of those conditions.

This invention also relates to a method for enhancing erythropoiesis in an animal, particularly a human, which comprises administering an effective dose of an EpoR monoclonal antibody having agonist activity. The mAb can include one or more of the engineered antibodies or altered antibodies described herein or fragments thereof.

In addition, the agonist monoclonal antibodies of the present invention can be co-administered with further active ingredients, such as other compounds known to enhance erythropoiesis or compounds known to have utility when used in combination with an EPO mimetic.

The therapeutic response induced by the use of the molecules of this aspect of the invention is produced by the binding to the EpoR and the subsequent agonist activity of the erythropoietic cascade. Thus, the molecules of the present invention, when in preparations and formulations appropriate for therapeutic use, are highly desirable for persons susceptible to or experiencing anemias, cytopenias and other conditions with depressed erythrocyte production.

This invention also relates to a method for decreasing erythropoiesis in an animal, particularly a human, which comprises administering an effective dose of an EpoR monoclonal antibody having antagonist activity. The mAb can include one or more of the engineered antibodies or altered antibodies described herein or fragments thereof.

In addition, the antagonist monoclonal antibodies of the present invention can be co-administered with further active ingredients, such as other compounds known to decrease erythropoiesis or compounds known to have utility when used in combination with a compound that decreases erythropoiesis.

The therapeutic response induced by the use of the molecules of this aspect of the invention is produced by the binding to the EpoR and the subsequent antagonist activity of the erythropoietic cascade. Thus, the molecules of the present invention, when in preparations and formulations appropriate for therapeutic use, are highly desirable for persons susceptible to or experiencing conditions with excessive erythrocyte production. Antibodies of this invention may become antagonist of the EpoR under certain circumstances including concentration.

The altered antibodies, antibodies and fragments thereof of this invention may also be used in conjunction with other antibodies, particularly human mAbs reactive with other markers (epitopes) responsible for the condition against which the engineered antibody of the invention is directed.

Agonist antibodies to the EPO receptor would have the same therapeutic utility as the natural ligand, but would have the advantage of longer half-life and hence prolonged activity in vivo. These agonists can thus be employed to activate the biological cascade which results from receptor/ligand binding. The advantages of EpoR agonist antibodies include the ability to administer lower dosages of antibody than ligand, easier and less frequent administration of a pharmaceutic based on the agonist antibody, as well as easier purification.

The EpoR agonist antibodies of the invention can be formulated into pharmaceutical compositions and administered in the same manner as described for mature proteins. See, e.g., International Patent Application, Publication No. WO90/02762 (Mar. 22 1990). Generally, these compositions contain a therapeutically effective amount of an agonist antibody of this invention and an acceptable pharmaceutical carrier. Suitable carriers are well known to those of skill in the art and include, for example, saline. Alternatively, such compositions may include conventional delivery systems into which protein of the invention is incorporated. Optionally, these compositions may contain other active ingredients, e.g., chemotherapeutics.

The therapeutic agents of this invention may be administered by any appropriate internal route, and may be repeated as needed, e.g., as frequently as one to three times daily for between 1 day to about three weeks to once per week or once biweekly. Preferably, the agonist antibody is administered less frequently than is the ligand, when it is used therapeutically. The dose and duration of treatment relates to the relative duration of the molecules of the present invention in the human circulation, and can be adjusted by one of skill in the art depending upon the condition being treated and the general health of the patient.

As used herein, the term "pharmaceutical" includes veterinary applications of the invention. The term "therapeutically effective amount" refers to that amount of a receptor agonist antibody, which is useful for alleviating a selected condition. These therapeutic compositions of the invention may be administered to mimic the effect of the normal receptor ligand.

The mode of administration of the therapeutic agent of the invention may be any suitable route which delivers the agent to the host. The altered antibodies, antibodies, engineered antibodies, and fragments thereof, and pharmaceutical compositions of the invention are particularly useful for parenteral administration, i.e., subcutaneously, intramuscularly, intravenously or intranasally.

Therapeutic agents of the invention may be prepared as pharmaceutical compositions containing an effective amount of the engineered (e.g., humanized) antibody of the invention as an active ingredient in a pharmaceutically acceptable carrier. In the compositions of the invention, an aqueous suspension or solution containing the engineered antibody, preferably buffered at physiological pH, in a form ready for injection is preferred. The compositions for parenteral administration will commonly comprise a solution of the engineered antibody of the invention or a cocktail thereof dissolved in an pharmaceutically acceptable carrier, preferably an aqueous carrier. A variety of aqueous carriers may be employed, e.g., 0.4% saline, 0.3% glycine and the like. These solutions are sterile and generally free of particulate matter. These solutions may be sterilized by conventional, well known sterilization techniques (e.g., filtration). The compositions may contain pharmaceutically acceptable auxiliary substances as required to approximate physiological conditions such as pH adjusting and buffering agents, etc. The concentration of the antibody of the invention in such pharmaceutical formulation can vary widely, i.e., from less than about 0.5%, usually at or at least about 1% to as much as 15 or 20% by weight and will be selected primarily based on fluid volumes, viscosities, etc., according to the particular mode of administration selected.

Thus, a pharmaceutical composition of the invention for intramuscular injection could be prepared to contain 1 mL sterile buffered water, and between about 1 ng to about 100 mg, e.g. about 50 ng to about 30 mg or more preferably, about 5 mg to about 25 mg, of an engineered antibody of the invention. Similarly, a pharmaceutical composition of the invention for intravenous infusion could be made up to contain about 250 ml of sterile Ringer's solution, and about 1 mg to about 30 mg and preferably 5 mg to about 25 mg of an engineered antibody of the invention. Actual methods for preparing parenterally administrable compositions are well known or will be apparent to those skilled in the art and are described in more detail in, for example, "Remington's Pharmaceutical Science", 15th ed., Mack Publishing Company, Easton, Pa.

It is preferred that the therapeutic agent of the invention, when in a pharmaceutical preparation, be present in unit dose forms. The appropriate therapeutically effective dose can be determined readily by those of skill in the art. To effectively treat anemia in a human or other animal, one dose of approximately 0.01 mg to approximately 20 mg per kg body weight of a protein or an antibody of this invention should be administered parenterally, preferably i.v. or i.m. Such dose may, if necessary, be repeated at appropriate time intervals selected as appropriate by a physician during the response period.

Optionally, the pharmaceutical compositions of the invention may contain other active ingredients or be administered in conjunction with other therapeutics. Suitable optional ingredients or other therapeutics include those conventional for treating conditions of this nature, e.g. EPO or other agents known for the treatment of anemias, cytopenias and other conditions with depressed erythrocyte production.

The present invention will now be described with reference to the following specific, non-limiting examples.

EXAMPLE 1

Preparation and Screening of EpoR Agonist Monoclonal Antibodies

Monoclonal Antibody Generation

Mice (F1 hybrids of Balb/c and C57BL/6) were immunised subcutaneously with 10 ug recombinant EpoR in Freunds complete adjuvant and 4 weeks later with 10 ug EpoR in Freunds incomplete adjuvant. On the basis of a good serum antibody titer to EpoR, one mouse received further immunization of 25 ug EpoR (i.p. in saline) at 8 weeks and another similar immunization two days later. A splenectomy was performed two days following the final immunization. Mouse spleen cells were used to prepare hybridomas by standard procedures, (Zola, H. Ed., Monoclonal Antibodies, CRC Press Inc. (1987)). Positive hybridomas were cloned by the limiting dilution method.

Hybridoma Screening Assay 96-well plates were coated with EpoR-Fc (0.5 ug/ml, 100 ul/well in PBS) by incubation overnight at 4° C. The solution was then aspirated and non-specific binding sites were blocked with 250 ul/well of 1% bovine serum albumin (BSA) in TBS buffer (50 nM Tris, 150 mM NaCl, 0.02% Kathon, pH 7.4) for 5–60 minutes at RT. Following this and each of the following steps, the plate was washed 4 times in wash buffer (10 mM Tris, 150 mM NaCl, 0.05% Tween 20, 0.02% Kathon, pH 7.4). To each well, 50 uL hybridoma medium and 50 uL assay buffer (0.5% BSA, 0.05% bovine gamma globulin, 0.01% Tween 40, 20 uM diethylenetriaminepentaacetic in TBS buffer) was added and the plates were incubated for 60 min at RT in a shaker-incubator, followed by an incubation of 60 min at RT in a shaker-incubator with 100 ul 0.5 ug/ml $Eu^{3+}$-labelled anti-mouse antibody in assay buffer. Finally, 100 ul/well of enhancer (Wallac) was added and incubated for 5 min at RT and the fluorescence measured. Hybridomas having counts >500 K were expanded into 24-well plates.

Immunoassay

To determine the specificity of the anti-EpoR mAbs generated, 96-well plates were coated (0.5 ug/ml EpoR-Fc, 100 ul/well) and blocked as above. All the following incubations were performed in a shaker-incubator at RT. After washing the wells 50 ul EpoR (3 ug/ml) or 50 ul assay buffer and 50 ul mAb were added and incubated for 60 min. After washing the wells 100 ul 0.5 ug/ml $Eu^{3+}$ labelled anti-mouse antibody in assay buffer was added for 60 min, the wells washed and then 100 ul/well of enhancer (Wallac) was added and incubated for 5 min at RT and the fluorescence measured. All positive hybridomas, including 3G9, showed displacement of binding with EpoR.

Selection of Antibodies by Flow Cytometry on UT7-Epo Cells

Flow cytometry was used to select hybridomas and primary clones that bind to the external domain of the wild type EpoR. A human megakaryoblastic cell line selected in Epo, UT-7-Epo, expresses the Epo receptor on its cell surface.

The mean and median values of fluorescent intensity were measured. Mean fluorescence is the average fluorescent intensity of a population of cells and the median intensity is the middle value between two extremes within the population. The fluorescence of 10,000 cells from each sample was measured. Monoclonal antibody 3G9, which bound to cell surface erythropoietin receptors, showed enhanced fluorescence over background and control monoclonal antibodies.

Purification of Mabs

Monoclonal antibodies were purified by ProsepA (Bio Processing Inc., Princeton, N.J.) chromatography respectively per the manufacturer's instructions. Mabs were >95% pure by SDS-PAGE.

EXAMPLE 2

Biophysical Characterization of EpoR Agonist Monoclonal Antibodies

Competition for Binding to EpoR with Epo

Antibodies were assessed for their ability to compete with Epo for binding to EpoRFc by surface plasmon resonance using a BIAcore instrument. Refractive index units (RU) increased for the sequential addition of EpoRFc, Epo and monoclonal antibody (or buffer), or the sequential addition of EpoRFc, mAb (or buffer) and Epo. The RU are a direct measure of the amount of each protein which can bind. Hence, prebinding of Epo reduces the amount of 3G9 which can bind. Similarly, prebound 3G9 is displaced by Epo which results in a negative change in RU.

Goat anti-human IgG, Fc specific antibody was immobilised on a sensor chip surface and 25 ul Epo-Rec-Fc (2 ug/ml diluted in HBS buffer) at 5 ul/min. was injected, the RU recorded, followed by injections of 25 ul Epo (5 ug/ml diluted in HBS buffer), record RU and 25 ul 3G9 Mab (10 ug/ml in HBS buffer), record RU. The surface was regenerated with an injection of 15 ul 0.1M phosphoric acid. The above was repeated reversing the order of addition for Epo and 3G9 Mab. These data showed that the monoclonal antibody 3G9 competed with Epo for binding to the erythropoietin receptor.

Affinity Measurements of 3G9 Monoclonal Antibody

The affinity of 3G9 was measured in the BIAcore. Using a flow rate of 5 ul/min, Mab 3G9 (diluted in HBS buffer) was injected over a rabbit anti-mouse Fc surface, followed by buffer flow and the RU recorded. EpoR or EpoRFc diluted in HBS buffer at 0.25–6 ug/ml was then injected for 120 s followed by buffer flow for 240 s and regeneration of the sensor chip surface with an injection of 15 ul 0.1 M phosphoric acid. BIAcore software was used for association and dissociation-phase analysis.

The parent murine monoclonal antibody, 3G9, and humanized and chimeric derivatives bound to soluble monomeric erythropoietin receptor (EpoR) with an on-rate ($k_{ass}$) of $1.0 \times 10^6$ $M^{-1}s^{-1}$ and an off-rate ($k_{diss}$) of $1.1 \times 10^{-3}$ $s^{-1}$. Together, these yield a calculated equilibrium constant ($K_D$) of 10 nM. The parent murine monoclonal antibody, 3G9, and humanized and chimeric derivatives bound to soluble dimeric erythropoietin receptor (EpoRFc) with an on-rate ($k_{ass}$) of $3 \times 10^6$ $M^{-1}s^{-1}$ and an off-rate ($k_{diss}$) of $1.9 \times 10^{-3}$ $s^{-1}$. Together, these yield a calculated equilibrium constant ($K_D$) of 0.6 nM.

EXAMPLE 3

Biological Activity of EpoR Monoclonal Antibodies Self-Limiting Effect

UT7-Epo Proliferation

UT-7Epo is a human cell line which depends on Epo for growth. Thymidine incorporation was used to measure proliferation of UT7-Epo cells. $5 \times 10^4$ cells in log phase growth were plated in 100 ul IMDM/10% FCS per well of a 96-well microtiter plate with test samples and Epo control curve. After a 3 day incubation at 37° C., $^3$H-thymidine (1 uCi/well; NEN) was added for 4 hrs and the plate harvested with TCA and cold ethanol. Solid scintillant (Meltilex; Wallac) was melted onto the filter containing the samples and radioactivity measured on a Betaplate reader (Wallac). Data were reported in FIG. 1 as the mean of quadruplicate samples.

The 3G9 mAb stimulated greater proliferative activity than the Epo control. Maximum proliferative activity was at 0.3 ug/ml and there was a bell-shaped dose response curve as concentration increased. The negative control antibody 3B3 had no activity in this assay.

Human CFU-E

Light density cells from human bone marrow centrifuged over Histopaque 1077 (Sigma) were washed and resuspended at $2.5 \times 10^6$ cells/ml in X-vivo medium (Biowhittaker). The purified monoclonal antibodies were diluted in X-vivo medium, and the Epo positive control was 2 U/ml/for the assay, 0.3 ml cells, 0.3 ml mAb sample (or Epo control) and 0.7 ml X-vivo medium were incubated in a polypropylene tube for 30 min at RT, then 0.9 ml FCS, 0.3 ml 10% BSA and 0.8 ml 3.2% methylcellulose were added. 0.4 ml were plated per well of a 24-well TC dish (Nunc). Colonies were identified microscopically as more than 8 red, hemoglobinized cells scored at day 7.

Figure 2:
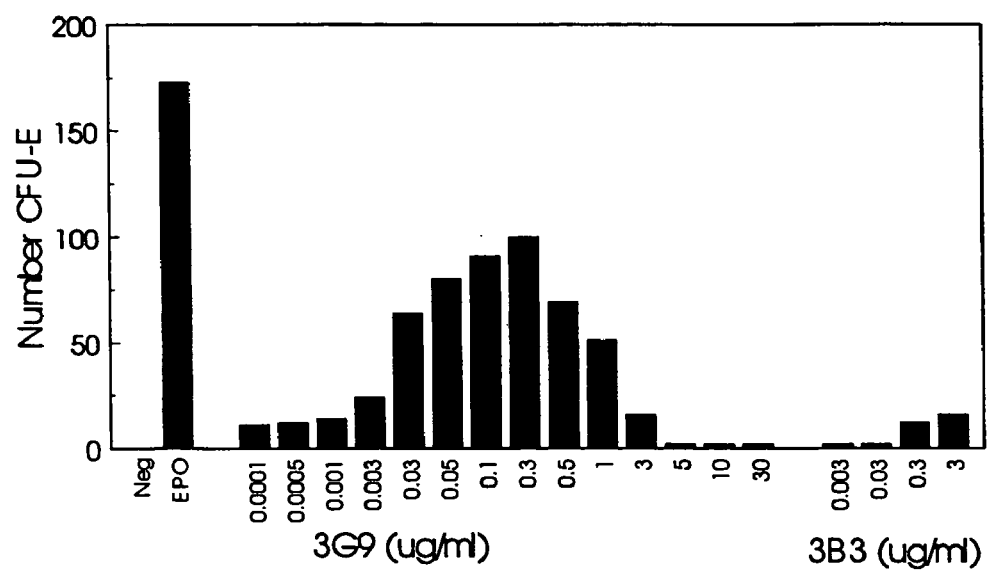
FIG. 2 is a graph of experimental results demonstrating the activity of monoclonal antibodies 3G9 and 3B3 in the human bone marrow CFU-E assay.

The results in FIG. 2 show that purified 3G9 mAb was most active at 0.3 ug/ml and has a bell-shaped dose response curve. The negative control antibody 3B3 had no significant activity.

Figure 3:
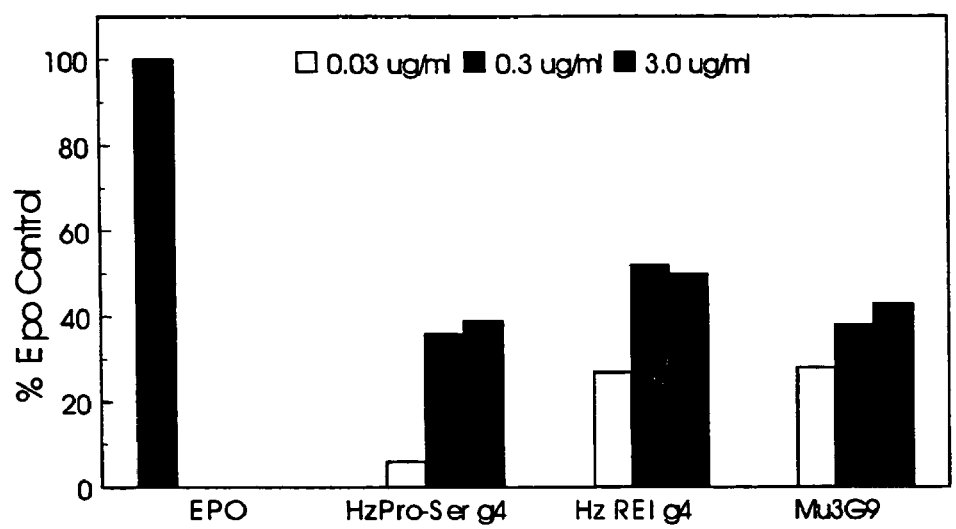
FIG. 3 is a graph of experimental results demonstrating the activity of humanized monoclonal antibodies 1-0 IgG4PE,REIk, S14 IgG4PE, 1-0k and 3G9 in the human bone marrow CFU-E assay.

The results in FIG. 3 show that the 3G9 humanized REI construct 1-0 IgG4PE,REIk (Hz REI g4) expresssed in CHO stimulated 52% of the number of colonies as a maximal amount of Epo. The humanized 3G9 pro to ser mutant S14 IgG4PE,1-0k (Hz Pro-Ser g4) expressed in COS cells had an equivalent number of colonies as the murine mAb (Mu3G9), 36 and 38% of Epo, respectively.

The HL5 humanized 3G9 construct 1-0 IgG1,5-0k had activity equal or greater than the murine 3G9 monoclonal antibody (57–68% of Epo control for HL5 vs. 55–58% for murine 3G9) in the human CFU-E assay (data not shown). The HL6 humanized 3G9 construct 1-0 IgG1,6-0k had approximately 25% of the Epo control activity in human CFU-E (data not shown).

Cross reactivity of an anti-human EpoR monoclonal antibody with various non-human EpoRs can allow the evaluation of 3G9 in vivo in the corresponding animal.

Primate CFU-E

Figure 4:
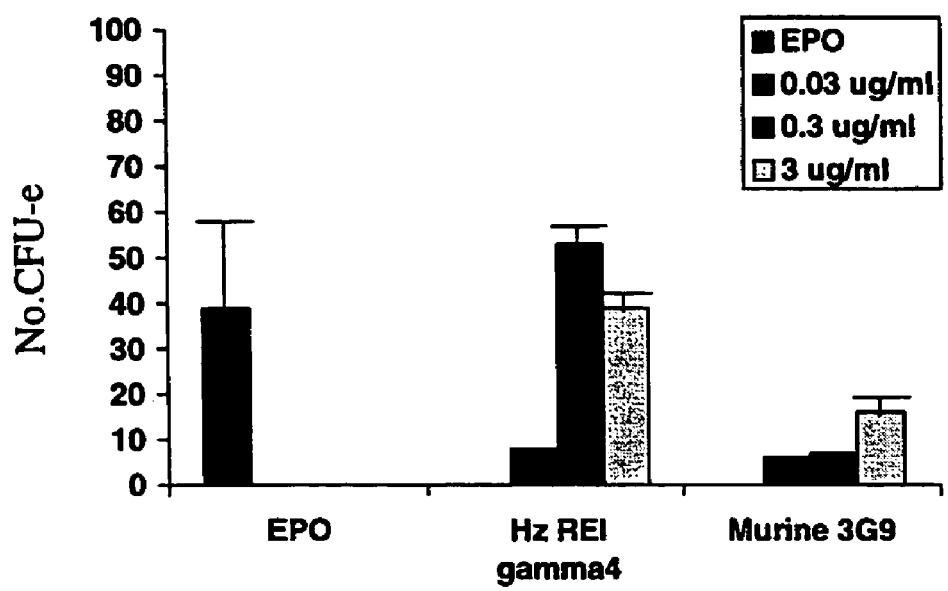
FIG. 4 is a graph of experimental results demonstrating the activity of humanized monoclonal antibodies 1-0 IgG4PE,REIk and 3G9 in the primate bone marrow CFU-E assay.

Primate marrow was prepared in the same way as human marrow. Marrow cells obtained from cynomolgus macaques were centrifuged on Histopaque 1066, washed and resuspended to $2.5 \times 10^6$ cells/ml. Epo control was 2 U/ml. The cells and antibody samples were incubated similarly, FCS, BSA and methylcellulose added and plated. Colonies were scored at day 7. FIG. 4 shows that the humanized 3G9 REI construct 1-0 IgG4PE,REIk (Hz REI gamma4) stimulated as many colonies as the maximal Epo control. The humanized 3G9 pro to ser mutant S14 IgG4PE,1-0k had an equivalent amount of CFU-E colonies stimulated as the murine 3G9 antibody (data not shown).

Rabbit CFU-E

Figure 5:
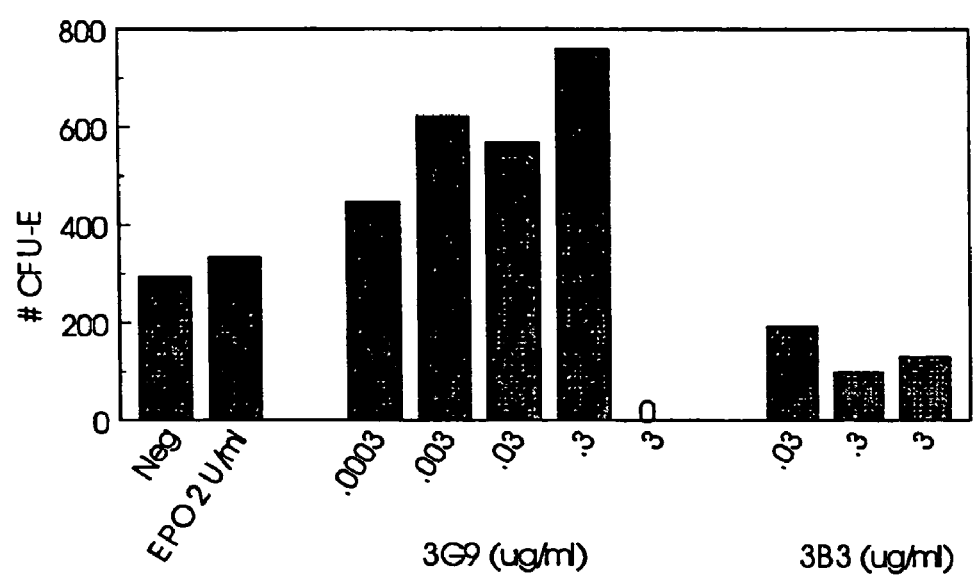
FIG. 5 is a graph of experimental results demonstrating the activity of Epo and the monoclonal antibodies 3G9 and 3B3 in the rabbit bone marrow CFU-E assay.

Rabbit marrow was flushed from the femur, washed and resuspended to $2.5 \times 10^6$ cells/ml. The cells were not centrifuged through Histopaque before addition to the antibodies. All other components and methods were similar to the human marrow. FIG. 5 shows that 3G9 had maximal activity at 0.3 ug/ml, with many more colonies than seen with Epo. The negative control antibody 3B3, which also binds to EpoR, had fewer colonies than the negative control.

Rabbit Reticulocyte Model

New Zealand White rabbits were injected i.v. with a single dose of 1 or 5 mg/kg murine 3G9 mAb, or i.v. with Epo (100 U/kg) 3 times per week. Blood samples were taken and reticulocytes were counted on a Sysmex reticulocytometer. As shown in Table 1 below 5 mg/kg murine 3G9 mAb elevated reticulocytes on day 5 significantly above the control.

TABLE 1

Effects on Rabbit Reticulocytes

| | Reticulocytes ($10^9$/L) Pre-dose | Reticulocytes ($10^9$/L) Day 5 | fold increase in reticulocytes |
|---|---|---|---|
| Control | 138.0 | 136.4 | 0.99 |
| Epo (100 U/kg) | 111.7 | 341.8 | 3.05 |
| Mu 3G9 mAb (5 mg/kg) | 135.9 | 200.1 | 1.47 |

Intracellular Signaling

Upon binding to its receptor, Epo stimulates the activation of an EpoR bound tyrosine kinase, JAK, through tyrosine phosphorylation, and the tyrosine phosphorylation of a latent cytoplasmic transcription factor, STAT5. Upon tyrosine phosphorylation, STAT5 translocates to the nucleus, and binds to regulatory regions of DNA, resulting in transcriptional activity of the associated gene. JAK activation was measured by immunoprecipitation with anti-JAK2 antibody and western blotting with anti-phosphotyrosine. UT7-Epo cells were grown in IMDM/10% FCS and starved of Epo for 24 hrs. The cells were then treated with Epo (0.1 and 1 U/ml) or monoclonal antibody 3G9 or 3B3 (0.003–3 ug/ml) for 10 min. After pelleting the cells, lysis buffer was added (0.05 M Tris-HCl, 1 mM sodium vanadate, 1 mM EDTA, 150 mM NaCl, 1% Triton X-100, 1 mM Pefabloc, 10 ug/ml aprotinin, 10 ug/ml leupeptin), and the samples incubated on ice for 20 min with occaisonal vortexing, after which the samples are centrifuged 1800 rpm for 3 min, 4° C. and the supernatents collected. Protein determinations were made with the BCA protein assay (Pierce, Arlington Heights, Ill.).

22.5 ug of each lysate was immunoprecipitated with 15 ug of agarose-conjugated JAK2 (UBI) for 1.5 hr at 4° C., centrifuged, and the pellet washed two times in cold lysis buffer. The pellet was then resuspended in SDS Tris-glycine sample buffer with 2.5% 2-mercaptoethanol and 20 ul run on a 8% Tris glycine gel. The samples were transferred to PVDF membranes and western blotted with anti-phosphotyrosine (1 ug/ml) for 1 hr using 0.5% gelatin/PBS-Tween-20 as the blocking buffer, HRP-labeled goat anti-mouse (Amersham, Rockford, Ill.) secondary antibody for 1 hr and detection using the enhanced chemiluminescence (ECL) reagents (Amersham).

Figure 6:
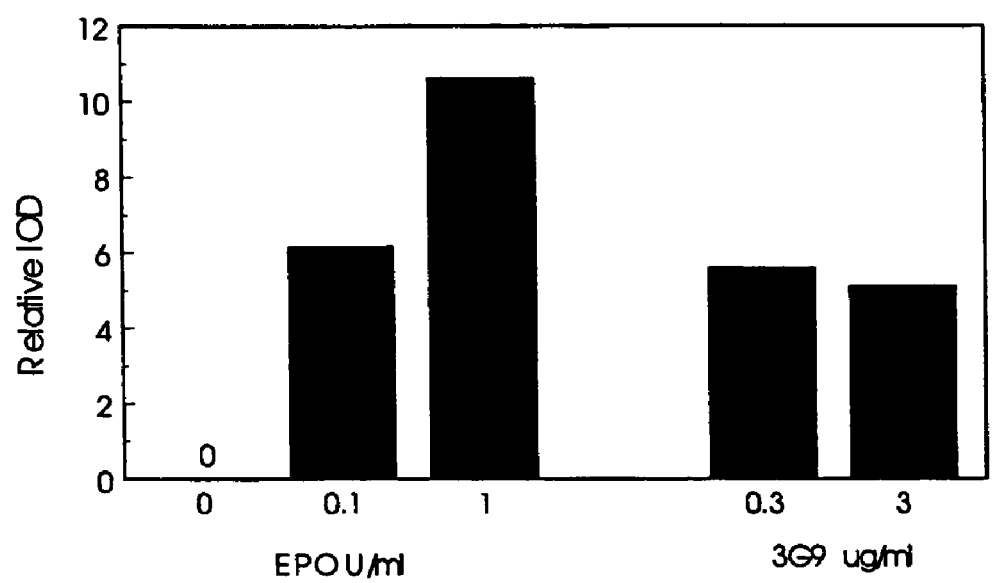
FIG. 6 is a graph of experimental results demonstrating JAK2 activation of UT7-Epo cells by Epo and the monoclonal antibody 3G9.
Figure 7:
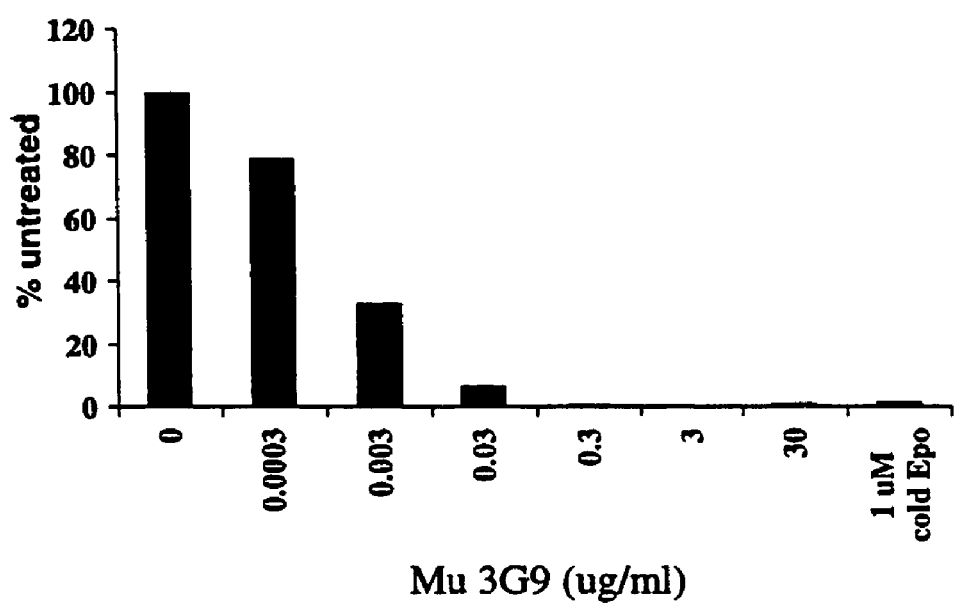
FIG. 7 is a graph of experimental results demonstrating the activity of murine 3G9 mAb competes with $^{125}$I-labeled Epo for binding to UT7-Epo cells. 1 nM $^{125}$I-labeled Epo (Amersham) and different concentration of 3G9 mAb or excess cold Epo were added simultaneously to $5\times10^5$ UT7-Epo cells. Following 5 hrs incubation at 4° C., the cells were spun through horse serum, frozen, and the pellets clipped off and radioactivity counted. Murine 3G9 antibody at 0.03–30 ug/ml inhibited Epo binding greater than 90%.
Figure 8:
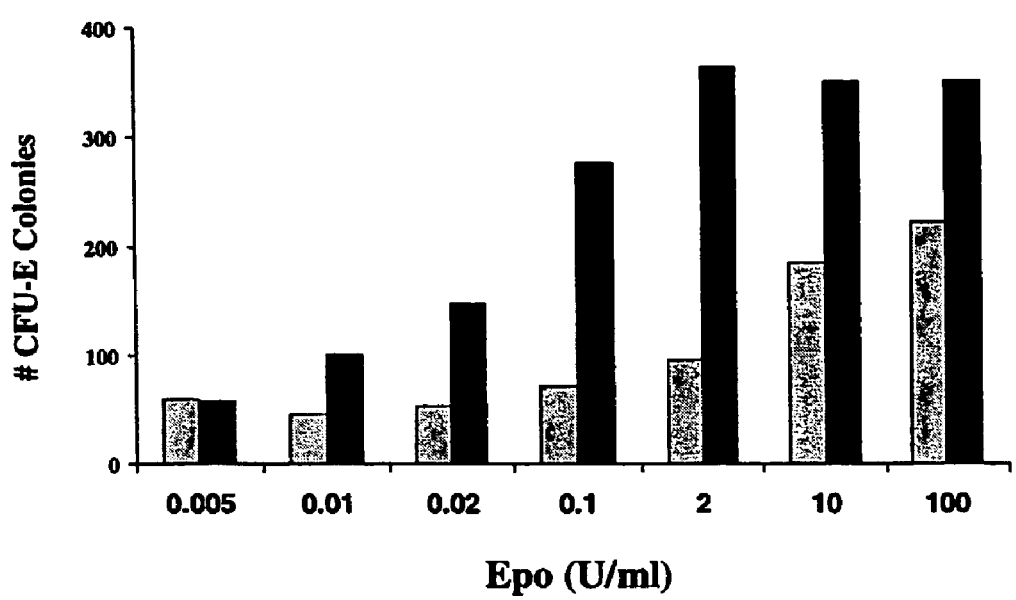
FIG. 8 is a graph of experimental results demonstrating the activity of inhibition of Epo-stimulated CFU-E by the presence of Hz3G9 mAb. Hz3G9 antibody at 30 ug/ml inhibited Epo-stimulated humna CFU-E at concentration of 0.005–100 U/ml. Hz3G9 was added to the marrow cell mix at the same time as Epo.
Figure 9:
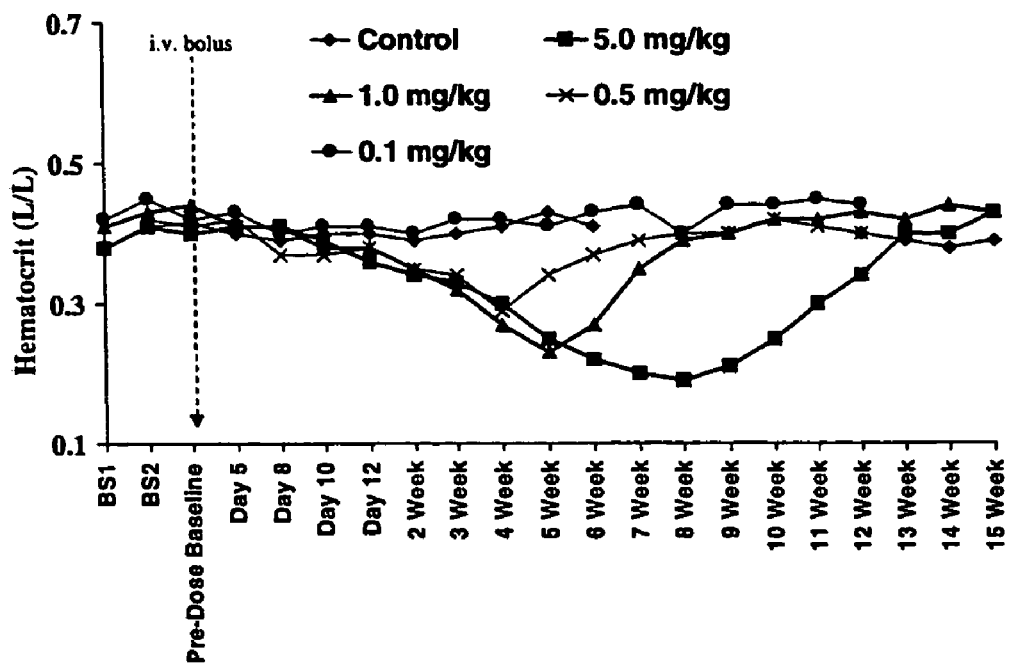
FIG. 9 is a graph of experimental results demonstrating the activity of inhibition of cynomolgus monkey hematocrit by single i.v. dose of Hz3G9. Hematocrit was measured following a single i.v. dose of Hz3G9 at 0.1, 0.5, 1 and 5 mg/kg into cynomolgus macaques. A dose dependent decrease in hematocrit was evident as early as day 10. The duration of hematocrit decrease was also dose dependent and lasted up to 13 weeks at the 5 mg/kg dose.

As shown in FIG. 6 below, 3G9 mAb induced activation (tyrosine-phosphorylation) of JAK2 with peak activation at 0.3 ug/ml mAb was equivalent to 50% of the maximum activation induced by Epo (1 U/ml). 3B3 did not activate JAK2.

EXAMPLE 4

Cloning and Sequencing of 3G9 Light and Heavy Chain cDNAs

The amino acid sequences of 13 light chain aminoterminal residues and 15 heavy chain amino-terminal residues of 3G9 were determined. The amino terminus of the heavy chain was blocked with pyroglutamic acid. It was successfully deblocked enzymatically using pyroglutamate aminopeptidase.

Total 3G9 RNA was purified, reverse transcribed and PCR amplified. For the heavy chain, the RNA/DNA hybrid was PCR amplified using a mouse IgG1 hinge primer and a degenerate primer based on the N-term protein sequence.

Similarly, for the light chain, the RNA/DNA hybrid was PCR amplified using a mouse kappa primer and a degenerate primer based on the N-term protein sequence. PCR inserts of the appropriate size, i.e., ~700 bp for the heavy chain and ~400 bp for the light chain were sequenced by a modification of the Sanger method. The sequence of 5 heavy and 4 light chain clones were compared to generate a consensus 3G9 heavy chain variable region sequence (SEQ ID NO: 1) and consensus 3G9 light chain variable region sequence (SEQ ID NO: 3). The heavy chain CDR 1, 2 and 3 amino acid sequences are shown in SEQ ID NOs: 5, 6 and 7, respectively. The light chain CDR 1, 2 and 3 amino acid sequences are shown in SEQ ID NOs: 8, 9 and 10, respectively.

EXAMPLE 5

Humanization of the 3G9 Antibody

Six humanized V region constructs were designed to contain the murine CDRs described above in a human antibody framework. In each case, the humanized $V_H$ and $V_L$ regions were first cloned into pCR2000 shuttle vectors, sequenced, corrected for mistakes, and then transferred to expression vectors as AgeI/KpnI and AgeI/ApaI fragments for $V_L$ and $V_H$ regions, respectively. The final humanized expression constructs encode complete heavy and light chains, comprising the initiation codon and the end of the Ck and $C_H3$ domains of the heavy and light chains, respectively.

1-0 IgG1,1-0k

The humanized antibody 1-0 IgG 1,1-0k contains the heavy chain V region 3G9HZHC 1-0 and the light chain V region 3G9HZLC 1-0.

The synthetic humanized heavy chain V region 3G9 HZHC 1-0 was designed using the homologous framework of the human $V_H$ subgroup I consensus sequence, generated from Kabat database sequences, and the 3G9 murine heavy chain CDRs described previously. Eight framework amino acids, which were predicted to influence CDR presentation, were substituted with the corresponding murine 3G9 residues. The construct 3G9HZHC1-0 includes the complete $V_H$ region and its sequence is shown in SEQ ID NO: 11.

The synthetic humanized light chain V region 3G9HZLC 10 was designed using the human kappa subgroup 1 framework consensus sequence and the 3G9 murine light chain CDRs described above. Three framework amino acids, which were predicted to influence CDR presentation, were substituted with the corresponding murine 3G9 residues. The construct 3G9HZLC 1-0 includes the complete $V_L$ region and its sequence is shown in SEQ ID NO: 15.

1-0 IgG4PE,1-0k

The humanized antibody 1-0 IgG4PE,1-0k contains the heavy chain V region 3G9HZHC 1-0 (SEQ ID NO: 11) and the light chain V region 3G9HZLC 1-0 (SEQ ID NO: 15). 3G9HZHC 1-0 (SEQ ID NO: 11) was inserted into an IgG4PE mutation expression vector.

S14 IgG4PE,1-0k

The humanized antibody S14 IgG4PE,1-0k contains the heavy chain V region 3G9HZHC S14 and the light chain V region 3G9HZLC 1-0 (SEQ ID NO: 15).

A variant of 3G9 HZHC 1-0 (SEQ ID NO: 11) was constructed containing a serine residue substituted for proline in the $V_H$ region at position 14. The sequence of the construct 3G9HZHC S14 is shown in SEQ ID NO: 13.

1-0 IgG1,REIk

The humanized antibody 1-0 IgG1,REIk contains the heavy chain V region 3G9HZHC 1-0 (SEQ ID NO: 11) and the light chain V region 3G9 HZLC 1-OREI.

A variant of 3G9HZLC 1-0 (SEQ ID NO: 15) was constructed using the framework residues of a derivative of the human light chain REI, REI-con (SEQ ID NO: 23). The framework of REI is very similar to that of the human kappa subgroup I consensus sequence used above for the construction of 3G9HZLC 1-0. In fact, only two residues of 3G9HZLC 1-0 were changed to generate 3G9HZLC-REI. Accordingly, as for 3G9HZLC1-0, three framework amino acids, which were predicted to influence CDR presentation, were substituted with the corresponding murine 3G9 residues. The construct 3G9HZLC 1-OREI includes the complete $V_L$ region and its sequence is shown in SEQ ID NO: 17.

1-0 IgG4PE,REIk

The humanized antibody 1-0 IgG4PE,REIk contains the heavy chain V region HZHC 1-0 (SEQ ID NO: 11) inserted into the IgG4PE expression vector and the light chain V region HZLC 1-OREI (SEQ ID NO: 17).

1-0 IgG1,5-0k

The humanized antibody 1-0 IgG1,5-0k contains the heavy chain V region HZHC 1-0 (SEQ ID NO: 11) and the light chain V region HZLC 5-0.

A variant of HZLC 1-0 (SEQ ID NO: 15) was constructed by site directed mutagenesis of HZLC 1-0 in which a single residue (Phe73) of the framework of a derivative of the human light chain REI, REI-con (SEQ ID NO 23) was introduced at position $V_L73$. The construct HZLC5-0 includes the complete $V_L$ region and its sequence is shown in SEQ ID NO: 19.

1-0 IgG4PE,5-0k

The humanized antibody 1-0 IgG4PE,5-0k contains the heavy chain V region HZHC 1-0 (SEQ ID NO: 11) inserted into the IgG4PE expression vector and the light chain V region HZLC 5-0 (SEQ ID NO: 19).

1-0 IgG1,6-0k

The humanized antibody 1-0 IgG 1,6-0k contains the heavy chain V region HZHC 1-0 (SEQ ID NO: 11) and the light chain V region HZLC 6-0.

A variant of HZLC 1-0 (SEQ ID NO: 15) was constructed by site directed mutagenesis of HZLC 1-0 in which a single residue (Ile83) of the framework of a derivative of the human light chain REI, REI-con (SEQ ID NO 23) was introduced at position VL83. The construct HZLCLC 6-0 includes the complete $V_L$ region and its sequence is shown in SEQ ID NO: 21.

1-0 IgG4PE,6-0k

The humanized antibody 1-0 IgG4PE,6-0k contains the heavy chain V region HZHC 1-0 (SEQ ID NO: 11) inserted into the IgG4PE expression vector and the light chain V region HZLC 6-0 (SEQ ID NO: 21).

EXAMPLE 6

Expression of Humanized 3G9 Antibodies in Mammalian Cells

The humanized heavy and light chains described above were expressed in expression plasmid derivatives of pCDN (A. Nambi, et al., (1994), *Mol. Cell. Biochem.*, 131:75–85). Accordingly, each expression plasmid variant contains, in general, a beta-lactamase gene, an SV40 origin of replication, a cytomegalovirus promoter sequence, a selected humanized heavy or light chain, a poly A signal for bovine growth hormone (BGH), a betaglobin promoter, a dihydrofolate reductase gene, and another BGH sequence poly A signal. These features are present in a pUC19 background for bacterial replication of the plasmid.

For initial characterization, the humanized 3G9 constructs were transiently expressed in COS cells essentially as described in Current Protocols in Molecular Biology (edited by F. M. Ausubel et al. (1988), John Wiley and Sons, vol. I, section 9.1). Briefly, COS cells were co-trnsfected with 10 micrograms each of heavy and light chain expression construct. After one day of culture, the growth medium was replaced with serum free medium, which was harvested and replaced on day three. Culture supernatant was again harvested on day five, and reserved for further analysis.

The present invention may be embodied in other specific forms without departing from the spirit or essential attributes thereof, and, accordingly, reference should be made to the appended claims, rather than to the foregoing specification, as indicating the scope of the invention.

What is claimed is:

1. An isolated erythropoietin receptor binding antibody comprising a $V_H$ amino acid sequence comprising the sequence of SEQ ID NO: 12 and a $V_L$ amino acid sequence comprising the sequence of SEQ ID NO: 16.

2. An isolated erythropoietin receptor binding antibody comprising a $V_H$ amino acid sequence comprising the sequence of SEQ ID NO: 12.

3. An isolated erythropoietin receptor binding antibody comprising a $V_L$ amino acid sequence comprising the sequence of SEQ ID NO: 16.

4. The antibody of any of claims 1–3 wherein the heavy chain constant regions are immuno-globulin class IgG, IgM, IgA or IgE.

5. The antibody of claim 4 wherein the heavy chain constant regions are subtype IgG1, IgG2, IgG3 or IgG4.

6. The antibody of claim 5 wherein the heavy chain constant region is an IgG4 subtype and comprises a serine to proline mutation at amino acid position 228 and a lysine to glutamic acid mutation at amino acid position 235.

7. An isolated erythropoietin receptor binding bivalent fragment of the antibody of claim 4.

8. A pharmaceutical composition comprising the antibody of any of claim 4 and a pharmaceutically acceptable carrier.

9. A pharmaceutical composition comprising the antibody of claim 5 and a pharmaceutically acceptable carrier.

10. The pharmaceutical composition of claim 9 further comprising an additional active ingredient.

11. The antibody of any one of claims 1–3 that is a monoclonal antibody.

12. The antibody of claim 5 that is a monoclonal antibody.

13. The antibody of claim 6 that is a monoclonal antibody.

14. The antibody of claim 8 that is a monoclonal antibody.

15. The antibody of claim 9 that is a monoclonal antibody.

16. The antibody of claim 10 that is a monoclonal antibody.

* * * * *